US006020318A

United States Patent [19]
Szyf et al.

[11] Patent Number: 6,020,318
[45] Date of Patent: Feb. 1, 2000

[54] DNA METHYLTRANSFERASE GENOMIC SEQUENCES AND ANTISENSE OLIGONUCLEOTIDES

[75] Inventors: Moshe Szyf, Cote St. Luc, Canada; Pascal Bigey, Clermont-Ferrand, France; Shyam Ramchandani, Montreal, Canada

[73] Assignee: MethylGene, Inc., Canada

[21] Appl. No.: 08/866,340

[22] Filed: May 30, 1997

[51] Int. Cl.[7] .............................. A61K 31/70; C07H 21/00
[52] U.S. Cl. .............................................. 514/44; 536/24.5
[58] Field of Search ................................ 435/6, 194, 375; 514/44; 536/24.3, 24.31, 24.5; 935/33, 34, 36

[56] References Cited

U.S. PATENT DOCUMENTS

| | | | |
|---|---|---|---|
| 5,578,716 | 11/1996 | Szyf et al. | 536/24.5 |
| 5,585,479 | 12/1996 | Hoke et al. | 536/24.5 |

FOREIGN PATENT DOCUMENTS

| | | |
|---|---|---|
| WO 92/15680 | 9/1992 | WIPO . |
| WO 95/15378 | 8/1995 | WIPO . |

OTHER PUBLICATIONS

Antisense '97: A roundtable on the state of the industry. Nature Biotechnol. 15: 519–524, Jun. 1997.
Gewirtz et al. Facilitating oligonucleotide delivery: Helping antisense deliver on its promise. Proc. Natl. Acad. Sci. USA 93: 3161–3163, Apr. 1996.
Gura. Antisense has growing pains. Science 270: 575–577, Oct. 1995.
Rojanasakul. Antisense oligonucleotide therapeutics: drug delivery and targeting. Adv. Drug Delivery rev. 18: 115–131, 1996.
Stull et al. Antigene, ribozyme and aptamer nucleic acid drugs: Progress and Prospects. Pharmaceutical Res. 12: 465–483, Apr. 1995.
Zon et al. "Phosphorothioate oligonucleotides" in Oligonucleotides and Analogues: A Practical Approach, Eckstein, ed. IRL press, New York, pp. 87–108, 1991.
Yen R.–W. C. et al., "Isolation and characterization of the cDNA encoding human DNA methyltransferase." Nucleic Acids Res. 20(9):2287–2291 (1992).
Yoder J. A. et al., "New 5' regions of the murine and human genes for DNA (cytosine–5)–methyltransferase." J. Biol. Chem. 271(49):31092–31097 (1996).
Yoder and Bestor, "Genetic analysis of genomic methylation patterns in plants and mammals." Biol. Chem. 377(10):605–610 (1996).
Ramchandani S. et al., "Inhibition of tumorigenesis by a cytosine–DNA, methyltransferase, antisense oligodeoxynucleotide." Proc. Natl. Acad. Sci. USA 94(2):684–689 (1997).
Ramchandani S. et al., "Genomic structure of the human DNA methyltransferase gene." Biol. Chem. 379(4–5):535–540 (1998).

Szyf, M. "The DNA methylation machinery as a target for anticancer therapy." Pharmacol. Ther. 70(1):1–37 (1996).
MacLeod and Szyf, "Expression of antisense to DNA methyltransferase mRNA induces DNA demethylation and inhibits tumorigenesis." J. Biol. Chem. 270(14):8037–8043 (1995).
Zhao Q. et al., "Effect of different chemically modified oligodeoxynucleotides on immune stimulation." Biochem. Pharmacol. 51(2):173–182 (1996).
Maniatis et al. (1987) Science 236:1237–1245.
Ingarham et al. (1990) Annual Review of Physiology 52:773–791.
Midgeon (1994) Trends Genet. 10:230–235.
Peterson et al. (1993) Ann. Rev. Genet. 27:7–31.
Holliday (1990) Trans. R. Soc. Lond. B. Biol. Sci. 326:329–338.
Lock et al. (1987) Cell 48:39–46.
Bartolomei et al. (1993) Genes Dev. 7:1663–1673.
Brandeis et al. (1993) Embo J. 12:3669–3677.
Szyf et al. (1995) J. Biol. Chem. 267:12831–12836.
Pon (1993) Methods in Molecular Biology 20:465.
Szyf et al. (1995) J. Biol. Chem. 270:12690–12696.
Freedman et al. (1974) Cell 3:355–359.
Meyer et al. (1989) Int. J. Cancer 43:851–856.
Rouleau et al. (1992) J. Biol. Chem. 267:7368–7377.
Razin et al. (1984) Biochim. Biophys. Acta. 782:331–342.
Li et al. (1992) Cell 69:915–926.
Szyf et al. (1985) J. Biol. Chem. 260:8653–8656.
Szyf et al. (1991) J. Biol. Chem. 266:10027–10030.
Ohtani–Fukita et al. (1993) Oncogene 8:1063–1067.
Feinberg et al. (1988) J. Can. Res. 48:1159–1161.
Goelz et al. (1985) Science 228:187–190.
Steinberg and Vogelstein (1983) Nature 301:89–92.
Agrawal (1992) Trends in Biotech 10:152.
Stepheneson et al. (1978) Procd. Natl. Acad. Sci. U.S.A. 75:285.
Leonetti et al. (1988) Gene 72:323.
Burch and Mahan (1991) J. Clin. Invest. 88:1190.
Jones et al. (1990) Adv. in Cancer Res. 54:1–23.
Szyf et al. (1989) Proc. Natl. Acad. Sci. USA 86:6853–6857.
Szyf et al. (1990) Mol. Enocrin. 4:1144–1152.
Zakut–Houri et al. (1983) Nature 306:594–597.

*Primary Examiner*—Nancy Degen
*Assistant Examiner*—Thomas G. Larson
*Attorney, Agent, or Firm*—Hale and Dorr LLP

[57] ABSTRACT

The invention provides recombinant nucleic acids comprising nucleic acid sequences from the genomic DNA methyltransferase gene. The invention further provides sequence information for such nucleic acid sequences. In addition, the invention provides antisense oligonucleotides complementary to special regions of the genomic DNA methyltransferase gene or its RNA transcript. Finally, the invention provides methods for using such antisense oligonucleotides as analytical and diagnostic tools, as potentiators of transgenic plant and animal studies and gene therapy approaches, and as potential therapeutic agents.

8 Claims, 15 Drawing Sheets

FIG. 1A

SEQ ID NO 1→
5'TCTAGAGCTCGCGGCCGCGACGTCAATTAACCCTCACTAAAGGGAGTCGACTCGA
TCGCCCTATGTTGTCCAGGGCTGGACTCGAACTCCTGCCCACAAGCCATCCTCCCAC
CACAGCCTCCTGAGTAGCTGGGGTTACAGGCACGCAGCACCGCGGCACTGCACCGGC
TTTTGTTCTTTTATTTTTTTCCCTCTTTGTCCCTGAAAGAGTCAAGCTACTAATTGT
CAGTAATCAAATCAGACCACGATTTCCCAGGCAAACTCCTGGCAGTTCTACATTTAG
GAATGACTAGCTAGAGACATCCTGAAGAATGAGTTATTCGGGGAGGCGCCACGACCT
CCTCTAACTTCACCTCTATCTGCCCTCTGTGTGGGTACCCCTTGCTTCCCTGGATGC
TTGACTCCCCCATTTCATCCTCAAAATGCCACCACCCCCACCAGGCCTTTAGGAAC
ATCAGCTGGCTGTTCCCCACAGTGTCCTGTGGCCCTGGGCTACTCATTCTGACACTG
GCCATACTGTGGCACACCTTGTTATGGGCTGTTGTCAGACCCAACTGGAGAAAGACC
AGCTGTAGGTCATTTCCCTTACGGGAGTGCCCCAACTATATGACCTGCCCCCTCTTT
CCTGGTATCTTTTTGAGTCAGGGTCTCACTCTGTCTCCTAGATTGGAGTGCAGTGAT
GCAATCACGGCTCACTGTGGCCTCGACCTCCCAGGCTCAGGTGATCTTCTTCTCAGC
CTCCCAAGTAACTGGGACCACAAGCACATGCCACCAAACCCAGTTATTTTTATTTTA
TTTTATTTTATTTTATTTTGAGACAGAGTTTCACTCTTGTTGCCCAGGCTAGAGTGC
AATGGTGTGACCAGCTCACTGCAACCTCTGCCTCCCGGGTTCAAGTGATTCTCCTGC
TCAGCCTCCAAGTTGCTGGGATTACAGCCACCCACCACCCACGCCTGGCTAATTTTT
GTATTTTTAGTAGAGATGGGGTTTCGCCATGTTGGCCAGGCTGGTCTCAAACCCTTG
ACCTCAGGTAATCCACCCACCTTGGCCCTCAGGTAATCCACCCAACTGCTGCTGTAT
GTTGGGATTCCAGGCATCAGCCACCACGCCCAGCCACTAATTTTTGTATTTTTGTAG
AGATGGAGTTTCGCCATGTTTCCCAGGCTGGTCTGAACGCCTGGGCTCAAGTGATCC
GCTCGCCTTGGCCTCCCAAAGAGCTGGGATTATAAGCGTGAGCCACCATGCCTGGTC
TCTGGTACCTTTTAAAATATACAGGCTGGGCATGATGGCTCATGCCTGTAATCCCAG
CACTTTGGGAGGCTGAGGCAGGTGGATCGCCTGAGGTCGGGAGTTCGAAACCTAGCC
TGACCAACACGGAGAAACCCTGTCTCTGCTAAAAATATAAAATTAGCTGGGTGATGG
TGGTGCATGCCTGTAATCCAGCTACTCGGGAGGCTGAGCCAGGAGAATCGCTTGAAC
CTGGGAGTCGGAGGTTTGAGCTGAGATCACACCATTGCACTCCAGCCTGGGCAACAA
GAGCAAAACCCTATCTCAAAAAAAAAAAATATATATATATATATATATATATATACA

FIG. 1B

CAGCTATATATAGCGTATATATATATACACACATATGTATACATATATACGTATG

TATACACATATATACGTATATATACACATATATATGTATATATACACACATATACGT

GTATATATATACGTGTATATATATATGCATGCCAGACAAGGTGACTCATGCCTGTAA

TCCTAGCACTTCAGGAGACTGAGGCAGGCGGATTCACTTGAGGTCAGGAATCTAAGA

CCAGGCTTAACCAACATGGTGAAACCCTGTCTCTACTCAAAATACAAAAAATTAACG

AGGCTGGTGGCACCTATAATCCCAGCTACTTGGGAGGGCTGAGGTGAGAGAATCACT

TGAACCCAGAAGGTGAGGGTTGCAGTGAGCTGAGATCGCACCACTGCACTCCACCTG

GGCAACAGAGCGAGACTCCATGTCTGTCTGTCTGTCTATCTATCTGTATAATGTATA

TGTATGTATGTATATATGTGTGTGTATATATATACACATATATACATACATATATAC

ACACATACTCTGTTACAGAGCTGCTGTGTGTGTGTGTATATATATATACACATATGT

ATATATACACATATACACATATATATGTATATATATACACACATATATATACACATA

TATATGTATATATATACACACATATATATACACATATATATGATATATATACACATA

TATATGTATATATATACACACACACACATACACATAATTGTGTTACAGAGCTGCT

ATGTAATCTCACAATCATCAGAAAAATGACCCCCAAAAGGGGAACCTTGTTCAGATC

AGATGACTTCTTAGCATTAGGCATTCCAGTAGGACACTCTAGACTCTTGCGGGGAGA

CAAAAGCCAGCTTAGTTTTTTCTAACACTCATATGTTAAACTTGTTTGTGTCCAAAA

CTTCTTTAGAACTGTGATATTCTTACAGGCAAATGAAGTTGCTTAACAAGTGTTTGT

ATTTTCTCCCCTATTTCTTCCTCCCAG$_{77}$GCTCAAAGATTTGGAAAGAGACAGCTTAA

CAGAAA$_{112}$AGGTAATCTCCTCCTTAAAATTTTTCTTATTACCAAATCTGACTGACAC

ACTTTGTGGCTCATAAAAAGAAATTTGTTTTCTTTAAATGGATTTTGCATTTTTTCC

CATGGAGTTTCAAAGATAATTTGGATATTCTTGTTAAATGTCAGCACTAATTTGCTG

CTAATAGTTGGGTGGTGGTGGTGTTTTTTTTTGTTGTTGTTTTGTTTTTTGAGACA

GAGTCTCACTCTGTCACCCAGGCTAGAGTGCAATGGCATGATCTCGGCCTCACTGTG

ACCTCTGCCTCCCGGATTCAAGCTGTTCTCCTGCCTCAGCCTCCCAAGTAGCTCTAA

CTACAGGCTCAAGCCACCATGCCCAGCTAATTTTTAAATATTTTTTGTAAAGATGGG

ATTTTGTCATGTTGCCCCAGGCTGGTCTTGAACTCTGGGGCTCAAAGCAATCCACTT

GCCTCGGCCTCCCAAAGTGCTGGGATTATAGGTGTGAGCCACTGTGCCTGGCCCVAS

GACATTTACAGAAGCACAGTATTATTCTTATAAACCATGATATGTCTCCATCTCACC

TCCAGCTTTCCCATTTTTCACCACTTTGGAGACAGGAGTGAAGTGATCCTAATGGAA

FIG. 1C

ATTCCCTGAACACATTTCATGACTGTTTAGTGTTTTGACTGAGACAGCATTGCCTGC

CATTCACTCATTGTGATGTGATCAGGCAGCTCAATAATTTGTGTATTAGTCCACTAG

TGAATAGCTTGGGAATGTGGGTACTGCTAAACCTATATCCTTCCCTTA<sup>113</sup>GGAATGT

GTGAAGGAGAAATTGAATCTCTTGCACGAATTTCTGCAAACAGAAATAAAGAATCAG

TTATGTGACTTGGAAACCAAATTACGTAAAGAAGAATT<u>ATCCGAGG</u><sup>223</sup><u>TAAGTCAGT</u>
                                              SEQ ID NO 33

<u>TCT</u>CAGCATCCTAGCCTCTAGAAAAATGTCTCCTCCTAGTAACTTGTCTGTGACCAG

GGAGGCAGCAAGATCCCCAGCTGTCCTCATTGCCTGATGATGATGATGATGATGATG

ATGATGAAGAACACATGTGTTCTGTCTCTGACACGTGTTACATTCACTGCTACTAAT

TATCCTGTCCTGCTGTAGGA<sup>224</sup>GGGCTACCTGGCTAAAGTCAAATCCCTGTTAAAT<u>A</u>

<u>AAGATTTTGTCCTTGAGAACGGTGCTCATGCTTACAACCGGAAGTGAATGGACGTCT</u>

<u>AGAAAACGGGAACCAAGCAAGAAGTGAAGCCCGTAGAGTGGGAATGGCAGATGCCAA</u>

<u>CAGCCCCCCAAACCCCTTTCCAAACCTCGCACGCCCAGGAGGAGCAAGTCCGATGG</u>

<u>AGAGGCTAAGC</u><sup>442</sup>GTAAGAGCAGATGATTCCTTTTATTTTTAATTGTTTTTGAGATG
  SEQ ID NO 57

GAGTCTCACTGTGTTGCCCAGTCTGGAGCACAGTGGTGTAACCTCGGCTCACTGTAA

CCTCTGCCTCCAGGTTCAAGAGACCCTCCTGCCTCAGCCTCCCAAGTAACTGnnn~
←SEQ ID NO 1   SEQ ID NO 2→
600bp~nnnGCCAACATTAGCAAGCTGGTTGTTGACTAGAATAAAAATGCAAAGAT

GCTAGTCCTTAGAACCTGGGCTTCCTGCAATAGCTTAGTAATGTTGAACTGCATTAT

TGCTGTGGGCTTTCTATTGATAGTGGCTTTTTTTTTCTTTTTAATGCTTTTTCTT<u>C</u>

<u>TTTAAACAGC</u><sup>443</sup><u>TGAACCTTC</u>ACCTAGCCCCAGGATTACAAGGAAAAGCACCAGGCA
SEQ ID NO 58

AACCACCATCACATCTCATTTTGCAAAGGG<sup>518</sup>GTCAGTATACGATAAATTGGCGGCT

GCCTTTTTTAGGGGCCGGCTGTTTTGGGATGGAATTGGTAGGGCGTCACGTGGCAAT
         ←SEQ ID NO 2           SEQ ID NO 3→
TCTGTCTTCCGTGTTGTATAnn~1000bp~nnnTCTCTGACACTAGCAGCTGTTG

ATCGGTGTTTAGACCCGTGATTTCTTAGGACTTACAAGATGGCAAGACAACATTCTA

AACCCGTCATTCAGAGAAACATTAAACTTGAAGCCTCTTTCAACATCCTGGTGAATG

AGGGTCCACTTCAGGCCAGCTGGAGGCCTAGGGTCTTGTTCCACTAATGGTTGGCCT

CACTGT<u>GTGTGACAGC</u><sup>519</sup><u>CCTGCCAAAC</u>GGAAACCTCAGGAAGAGTCTGAAAGAGCC
      SEQ ID NO 59

AAATCGGATGAGTCCATCAAGGAAGAAGA<u>CAAAGACCAGG</u><sup>598</sup><u>TAGGGCCAGTGCTTT</u>
                              SEQ ID NO 60

CATTTCCTGACTCTACCTTACTTGGTGTATTTGATGATTGTGACTTCATATGTGTTC

FIG. 1D

```
TGTCCAAGTAAATAAAAACCCTGTCTAGGGCTCTATTTAGGGCTCTCCAGAGACA
                    ←SEQ ID NO 3              SEQ ID NO
GGACCAATAGAATGTATATGTGTGTATCAACGTATAGnnnn~1500bp~nnnnGT
4→
TTTGGGGTTGGTGGGGATTAATACCAGAGTAAGAGTTTCTCAGATCTTCTCCCCTTT

TCCCAGGCCCCTTCTTTTCCCACTCTTGCTCTAACCATGTCAAATGTGTTAATATTT

CAACTCACACTTTTGGTGTTGACCTTCCCTTGAAACCAGTATTCTAATCTTTTTGT
                                          ←SEQ ID NO 4
TCTTCCTTCCCTCCACACAGGA   TGAGAAGAGACGTAGAGTTACATCCAGAGAAC
                      599                                 631
             SEQ ID NO 5→
nnn~700bp~nnnCAGGGCTCCGAGATAAGTAAGATTGCTTTTGGGGAAAAGAGGAG CTTTATGAAAACTGCTTCTTTGGGGAAGCTCCTGGCACTCACACTTGGGGTCTGTGT
             SEQ ID NO 61
TATTTTGCTTGACAG  AGTTGCTAGACCGCTTCCTGCAGAAGAACCTGAAAGAGCA
              632
                                              SEQ ID NO 62
AAATCAGGAACGCGCACTGAAAAGGAAGAAGAAAGAGATGAAAAAG  TAAAGCTCT
                                                      718
   ←SEQ ID 5         SEQ ID 6→                 ←SEQ ID 6
ATCACCTCTAAGnnnnnnA  AGAAAAGAGACTCCGAAGTCAAACCAAAGAACC  n
                 719                                   752
             SEQ ID NO 7→
nn~1000bp~nnTGAGTCCTGAGTAGTAAATCGTCTGGCTTCCTGCAGTGAAGAC

AGGAGAGGCAGCCTGTCCTCTGAACCTGGGGAGGAGCTTGTGTCAGCCCTTAGGAGC

TGTTGGCCCCGGTGCAGGGCCCCCCCCGAGCTGACCAGCCTGTGTGTGTGTTGTCTT
       SEQ ID NO 63
CTGTGACAGA  ACACCCAAACAGAAACTGAAGGAGGAGCCGGACAGAGAAGCCAGG
         753

GCAGGCGTGCAGGCTGACGAGGACGAAGATGGAGACGAGAAAGATGAGAAGAAGCAC
         ←SEQ ID NO 7        SEQ ID NO 8→
AGAAGTCAACCCAAAGATCT   nnnnGTGGTTAGTGTTTCTAAGCTGCTACTTGCTG
                    875
          SEQ ID NO 64
TGTATCTGTTCACCCTGCAGA  GCTGCCAAACGGAGGCCCGAAGAAAAAGAACCTG
                    876
                              ←SEQ ID 8   SEQ ID 9→
AAAAAGTAAATCCACAGATTTCTGATGAAAAAGACGAGGATGAAAAnnnnGGAGGAG AAGAGACGCAAAACGACCCCCAAAGAACCAACGGAGAAAAAAATGGCTCGCGCCAAA
       ←SEQ ID NO 9    SEQ ID NO 10→
ACAGTCATGAACTCCA   nnnnGCTCACGAGGCGGCTGGGAGCTGCTCTCTGAGTG
              1036
                 SEQ ID NO 34
CCATCATCTGTGTTCCTGCTCCCACA  GACCCACCCTCCCAAGTGCATTCAGTGCG
                         1037          ←SEQ ID NO 10
GGCAGTACCTGGACGACCCTGACCTCAAATATGGGCAGCACCCACCAGACGC  nn
  SEQ ID NO 11→                                     1118
nnG   GTGGATGAGCCACAGATGCTGACAAATGAGAAGCTGTCCATCTTTGATGCC
   1119

AACGAGTCTGGCTTTGAGAGTTATGAGGCGCTTCCCCAGCACAAACTGACCTGCTTC
   1229                                        ←SEQ ID
AG    GTAAGTGCACTTTCGTGTGCATGTTTGCTTCGTGGAAGGAGGCACATCCCAG
NO 11   SEQ ID NO 12→
AGGnnnnCCTCGTGCCTGATATGAAGTCTGCACGAAGACGCCCTTCACGGCTTAGCT
```

FIG. 1E

```
GGTAAGCATGTGCTTTGTTTCCTGTCTAGT  GTGTACTGTAAGCACGGTCACCTGT
                       1220
                     SEQ ID NO 35
GTCCCATCGACACCGGCCTCATCGAGAAGAATATCGAACTCTTCTTTTCTGGTTCAG

CAAAACCAATCTATGATGATGACCCGTCTCTTGAAGGT    AAGGAATAGTCCGGGAT
                                    1350
TATGTTTGGGGCACACTTTAAAAACAGCCAGGCAGGTTGGCTCACATCTGTAATCCT
                                 ←SEQ ID NO 12
AGCACTTTGGGGGCTGAGGCCAGAGGATCACTTGAGCCCGGGAGTTTnn~450bp~n
SEQ ID NO 13→
nTTTAGTCCATTTCCTTTTTCTGCTCTAGGTG    GTGTTAATGGCAAAAATCTTGGC
                               1351
CCCATAAATGAATGGTGGATCACTGGCTTTGATGGAGGTGAAAAGGCCCTCATCGGC
     SEQ ID NO 36
TTCAGCACCT   GTAAGTGTGTGGCCCATCATAGGCTGGCCGGGGTCTGAAAGGGGC
           1441
CTTCATGTTCTCCTTCCTGGGGCTGACGGGCTCTGGTGGGAATTCTCAGCAGGCT

TGCAGAAGGCCATGTGACTGGGAACCTTAGCAGGTTCAGTTGGGGTAGATCTCTTGT
       ←SEQ ID NO 13       SEQ ID NO 14→
GTTAGTTAGTAGGnnn~900bp~nnnCGCTCTCTGGCTGGCTCAGACAGGCTTCT

TCAGAACAAGCCAGCTATGATGTGTTGTGCCCTATGTTTCTGACATTTGGGTACGGG

ATGACTTTTAGACTGTTGGGTGAGTTTGGTAGACTCCTCCATGCCCTGTGGCCACTG

TAGGCGCCATCAGATTCCAGCCCCTTTTCCACACCTCCTCTGTTCGCCCCAGC  AT
                                                     1442
TTGCCGAATACATTCTGATGGATCCCAGTCCCGAGTATGCGCCCATATTTGGGCTGA

TGCAGGAGAAGATCTACATCAGCAAGATTGTGGTGGAGTTCCTGCAGAGCAATTCCG
                               SEQ ID NO 37
ACTCGACCTATGAGGACCTGATCAACAAGATCGAG   GTAAGAGATCGAGGGTCCTC
                                    1593
AGCATCCGGGATTCCCACTGGAAACTTGCCTTCAGAACCAGCAGACACTGTTCTTCA

GTTGGATTTAGGCCAGTTTGGCTTAAGCATGAGAGAAACCTGTTCTCTTTCAAGA
                                                       1594
CCACGGTTCCTCCTTCTGGCCTCAACTTGAACCGCTTCACAGAGGACTCCCTCCTGC

GACACGCGCAGTTTGTGGTGGAGCAGGTGGAGAGTTATGACGAGGCCGGGGACAGTG

ATGAGCAGCCCATCTTCCTGACGCCCTGCATGCGGGACCTGATCAAGCTGGCTGGGG
        SEQ ID NO 38
TCACGCTGGGACAGAGG   TAAGGATGCGGCTGGGACCAGAGTGAAGACTGGAGACC
               1782
GGGGAGGGTAGAGCATGGCCCACATCCTCTGTCCCAGTCCTCTGAGATGCTGGAACC

TCTCCCGTAGGC   GAGCCCAGGCGAGGCGGCAGACCATCAGGCATTCTACCAGGA
            1783
GAAGGACAGGGGACCCACGAAAGCCACCACCACCAAGCTGGTCTACCAGATCTTCGA

TACTTTCTTCGCAGAGCAAATTGAAAAGGATGACAGAGAAGACAAGGAGAACGCCTT
                                SEQ ID NO 39
TAAGCGCCGGCGATGTGGCGTCTGTGAGGT   AACCTCACCTGTGGGTGCTCCCGCT
                             1970
```

FIG. 1F

CCCCTAAGGTGGCCCAGCCTCTGGCCTGATCTGAGGACTGCTCCATCTTTCTCTGTG
                                             ←SEQ ID NO 14
GCTTGAGACTCTGGCTGCTCAAATGTGACCCTGAGACAGAAATTGTTGTGGnnnnAG
SEQ ID NO 15→
GTG    TGTCAGCAGCCTGAGTGTGGGAAATGTAAAGCCTGCAAGGACATGGTTAAAT
   1971
TTGGTGGCAGTGGACGGAGCAAGCAGGCTTGCCAAGAGCGGAGGT    AGGTCAGGCC
                                    SEQ ID NO 40    2068
GAGTCTTCCTCCTGTGGCAGAGGACTTGCCAGCTGGTGGCAGATGCACTGTGGAGAA
                              ←SEQ ID NO 15          SEQ ID NO
GGGCCGTCATGTGTGGACAGCACCAGGATTCCTTCGnn~180bp~nnAGACCTG
16→
TCCCTGTTATGAAGAAAACAGCCCCGGTTGGTCTTACTTAGAAAAGGGGCCTTAGGT
ATAACCAGTGACATTGCAGGTG     TCCCAATATGGCCATGAAGGAGGCAGATGACGA
                     2069
TGAGGAAGTCGATGATAACATCCAGAGATGCCGTCACCCAAAAAAATGCACCAGGG
                                                  SEQ ID NO 41
GAAGAAGAAGAAACAGAACAAGAATCGCATCTCTTGGGTCGGAGAAGCCGTCAAG
                                                         2214
                  ←SEQ ID NO 16          SEQ ID NO 17
GTAACCCTTGGAGTCCCCTTGGTTCAGTCCTCACTGCnn~1500bp~nnAAGTCA
→
AGGCCAGCAAAGACCCTCAGAATGATCCTCCATGAACTTATGCTCTCATTTTCAGA
 22
  CTGATGGGAAGAAGAGTTACTATAAGAAGGTGTGCATTGATGCGGAAACCCTGGAA
15
GTGGGGACTGTGTCTCTGTTATTCCAGATGATTCCTCAAAACCGCTGTATCTAGCA
SEQ ID NO 42
AGG    TTTGCATCTTTCTTTTTGCTTGACTTCTGCATGCACTTTCTCATCAAGTAGG
    2331
       ←SEQ ID NO 17          SEQ NO 18→
AGATGCCCTGTnn~150bp~nnCTCCCCATGCCCGTCTTCTATTCCAGGG    TCA
                                                  2332
CGGCGCTGTGGGAGGACAGCAGCAACGGGCAGATGTTTCACGCCCACTGGTTCTGCG
CTGGGACAGACACAGTCCTCGGGGCCACGTCGGACCCTCTGGAGCTGTTCTTGGTGG
ATGAATGTGAGGACATGCAGCTTTCATATATCCACAGCAAAGTGAAAGTCATCTACA
                                                  ←SEQ ID NO 18
AAGCCCCCTCCGAAAACTGGGCCATGGAGG    TGAGTGCCTGGTGTCCTCGTGAGCC
                              2536    SEQ ID NO 43
   SEQ I  NO 19→
CnnnnnGACCCAACCGACGATATCTTTGAGTCTCCCAAGGG    AGGCATGGATCCCG
                                         2537
AGTCCCTGCTGGAGGGGACGACGGGAAGACCTACTTCTACCAGCTGTGGTATGATC
AAGACTACGCGAGATTCGAGTCCCCTCCAAAAACCCAGCCAACAGAGGACAACAAGT
     SEQ ID NO 44
TCAA    GTGAGCACTGGGGCTGGACTCGGGGTCAGCAGGCACTTTCAGCCCACATCA
    2669
            ←SEQ ID NO 19        SEQ ID NO 20→
CTCCCTTTTCCCGTGTGCTTCCGnn~850bp~nnAAGCTGGCAGTAGCTGCTGCG
                                                 SEQ ID NO 45
GCCACTGCCGGCCACCTCAGGGCCTTATGTTTCTGTCCCTTTGTTTCCTTCAGA    T
                                                      2670
TCTGTGTGAGCTGTGCCCGTCTGGCTGAGATGAGGCAAAAAGAAATCCCCAGGGTCC

FIG. 1G

TGGAGCAGCTCGAGGACCTGGATAGCCGGGTCCTCTACTACTCAGCCACCAAGAACG

GCATCCTGTACCGAGTTGGTGATGGTGTGTACCTGCCCCCTGAGGCCTTCACGTTCA

A²⁸⁴³GTAAGTGCCCCCTCGGAGCAGCCGGGGCCAGGGGnn~450bp~nnAAATCAT
  ←SEQ ID NO 20            SEQ ID NO 21→

TTCTTAGGGTACACACCTACCTTAATTCATCAGGTGCTTGACTTTAAATGGTTATTT

TCACTGGTCAGTCATGCCTGACTGACCACTGCAAGGTGGAAGGTTCATTGATGTCAA

GTGGGTG<u>CTTCTCTGCAGC</u>  ATCAAGCTGTCCAGTCCCGTGAAACGCCCACGGAAG
        SEQ ID NO 46  2844

GAGCCCGTGGATGAGGACCTGTACCCAGAGCACTACCGGAAATACTCCGACTACATC

AAAGGCAGCAACCTGGATGCCCCTGAGCCCTACCGAATTGGCCGGATCAAAGAGATC

TTCTGTCCCAAGAAGAGCAACGGCAGGCCCAATGAGACTGACATCAAAATCCGGGTC

AACAAGTTCTACAGG     TCAGCAGAGGCCTCTGTTCTTCCTCGAGGCCACAGACTCT
              3066   SEQ ID NO 21       SEQ ID NO 22→
TCTAGAAGGCTCTGCTGAAACAAGGTTGTGGnn~520bp~nnAAAAGGAGAGCTC

CTAACGAGGCCTACTCCCGCTCGCAGGC   CTGAGAACACCCACAAGTCCACTCCAG
                            3067

CGAGCTACCACGCAGACATCAACCTGCTCTACTGGAGCGACGAGGAGGCCGTGGTGG

ACTTCAAGGCTGTGCAGGGCCGCTGCACCGTGGAGTATGGGGAGGACCTGCCCGAGT

GCGTCCAGGTGTACTCCATGGGCGGCCCCAACCGCTTCTACTTCCTCGAGG   TGGT
                                                   3259
GCCCCTGCTTGCTAGAGGGAAGGCTTCGGGGTCAAAGTTGGCCAGAAGGAGTCTGAT

GTCGGGTTATACACAAGGCGGCTTGGCTGCAGGGTTTCAGCTTTTGTAAGAAGTGGG

←SEQ ID NO 22
TGGTTGGCTGACGTGAAGCTGTTCTGCAGGAGCTTTACGGGGGnn~950bp~nnG
SEQ ID NO 23→
TCAACTACTCTATTGGTGGCTAATTGGTCATGGCCCCACTGAGGAGAATTAAGTGAC

TATCAATTGCCTTCTTACTAGTCTGCGTTAGAGAGGGGACAGTGGCGTTTCTCTCCC

AAACGATTGCAGTTCTCTCCTTTTCAGGC   CTATAATGCAAAGAGCAAAAGCTTTG
                            3260
AAGATCCTCCCAACCATGCCCGTAGCCCTGGAAACAAAGGGAAGGGCAAGGGAAAAG

G   TACGTCATTGTATGAGTTTCTTTTCAAGTTATTCTTCTGTAACTTGGAGGCTGC
 3344
CTGTGAATCCCTCAGTGTAAAACCACCTCTGGTGTTACTGACTCTGGGACAGCGAGG

CCGCCTGAGTTAACAAGGCGCTTGAGAGCAAGGTGGACTTGGACTCTGAGGATCGGG

SEQ ID NO 48
TTTAGCCTCTGGCCTCT<u>CTCCCCAGGG</u>  <u>AAGGGCAAG</u>CCCAAGTCCCAAGCCTGT
                         3345

GAGCCGAGCGAGCCAGAGATAGAGATCAAGCTGCCCAAGCTGCGGACCCTGGATGTG

SEQ ID NO 49
TTTTCTGGCTGCGGGGGGTTGTCGGAGGGATTCCA<u>CCAAGCAGG</u>  <u>TGAGCGCCGT</u>
                                              3473

AGGCTCCATCTCTGAATACCTGGTGAGCCCAGACCGGGCAGGTGCTACCTGAAACGA

FIG. 1H

←SEQ ID NO 23
CTTCCAACCCGGTCACCTTCTGATCTAAGAATCTCTTCGAGGCCAGGCACGnn~50
SEQ ID NO 24→
0bp~nnACTGCACGCCAGCCTGGGTGACAGAGCGAGACTCCATCTCAAAAAAAA

AAAAAAATCTTCTGGAGAGTTGAAAGCATGGCTTCGTGCTTGATCTGCCAGC$_{3474}$ATC

TCTGACACGCTGTGGGCCATCGAGATGTGGGACCCTGCGGCCCAGGCGTTCCGGCTG

AACAACCCCGGCTCCACAGTGTTCACAGAGGACTGCAACATCCTGCTGAAGCTGGTC

ATGGCTGGGGAGACCACCAACTCCCGCGGCCAGCGGCTGCCCCAGAAGGGAGACGTG

GAGATGCTGTGCGGCGGGCCGCCCTGCCAGGGCTTCAGCGGCATGAACCGCTTCAAT

TCGCGCACCTACTCCAAGTTCAAAAACTCTCTGGTGGTTTCCTTCCTCAG$_{3755}$GTAAA

CGGGTAGAAGCCCCCAGTGTTGCCAGACGGCCCGGGGCTGTGCGCATGTCAGCAGT

←SEQ ID NO 24    SEQ ID NO 25→
GTCATTTnn~250bp~nnnGAAGCTCACAGCTCAGCTCTCACCAGGGAGAGACTT

TGATAACATTCGTGAGGGGCTTCCGGCACAGTGGGCGTTTCTTCCCTCTGTCTGTGG

AGGTGACTCCTGCAGTCTCTCCTGCCCCTACAGCAGC$_{3756}$TACTGCGACTACTACCG

GCCCCGGTTCTTCCTCCTGGAGAATGTCAGGAACTTTGTCTCCTTCAAGCGCTCCAT

GGTCCTGAAGCTCACCCTCCGCTGCCTGGTCCGCATGGGCTATCAGTGCACCTTCGG

CGTGCTGCAGG$_{3898}$TGGGCCCTGGGGCTGGGCGGGCAGACAGATGAGGCCAGCACGT

GACCCGGCCAGCAGCCAGCCATCCCTTACTGAAGGCAGGGTTCAATGGCATAGGCCT

←SEQ ID NO 25
GCCATCCAGGCAGCAGAGGCTGGCATGGTGCTCTGTCCACTGGCGGATGAGGGGAGA
SEQ ID NO 26→
TCGnn~1200bp~nnCGACTCAGCTGCTGACCCTGGGCCTGGGTCTGGCCAGTCC

SEQ ID NO 50
AGTTGGGAGTGTCCCACTGACGGTGGGGTTGTCCGTCC<u>TTCTCCCCCACAGGC</u>$_{3899}$CG

<u>GTCAGTAC</u>GGCGTGGCCCAGACTAGGAGGCGGGCCATCATCCTGGCCGCGGCCCCTG

GAGAGAAGCTCCCTCTGTTCCCGGAGCCACTGCACGTGTTTGCTCCCCGGGCCTGCC

SEQ ID NO 51
AGCTGAGCGTGGTGGTGGATGACAAGAAGTTTGTGAGCAA<u>CATAACCAGGT</u>$_{4066}$AGGT

←SEQ ID NO 26
GGCCCCCGTCGCTCCTCCACACACTGCCGACGAGGCCTCAGTAGCTCATGGGGnn~6

SEQUENCE ID NO 27→
00bp~nnCATAGCCCCATCCCCCCTTCCAGATGGCATCCAGCACACTGCCACCCAT

GTGACCTCGGGCAGTGCTGTGATCTCGGGAGAAGGCCATCTGAGCAGGCAGGGGGTG

GCACCTGTGATGAGGGGACAGCTGCTGCGTGCATCTCCAGAGGTGTTGACCTCCTCC

TCTGTTGCAGGTT$_{4067}$GAGCTCGGGTCCTTTCCGGACCATCACGGTGCGAGACACGAT

GTCCGACCTGCCGGAGGTGCGGAATGGAGCCTCGGCACTGGAGATCTCCTACAACGG

FIG. 11

```
GGAGCCTCAGTCCTGGTTCCAGAGGCAGCTCCGGGGCGCACAGTACCAGCCCATCCT
              SEQ ID NO 52
CAGGGACCACATCTGTAAGG   TAATGGCACCCTGACAGAGCGGCTCCTCCTCGAGG
                 4243

CCCAGCCCAGCAGCCTCGTGGGAACAGTCAGCCTGCCCAAGACTCAGGGGAGACATG
                                     ←SEQ ID NO 27
GAATCTGATCCCAGGCTCCTCCTCCGAGTCTCAGCCTTTGTGTGAnn~600bp~n
SEQ ID NO 28→
nnATGGACACGTCCCCCCACACTCTTTCAGGA   CATGAGTGCATTGGTGGCTGCC
                              4244

CGCATGCGGCACATCCCCTTGGCCCCAGGGTCAGACTGGCGCGATCTGCCCAACATC

GAGGTGCGGCTCTCAGACGGCACCATGGCCAGGAAGCTGCGGTATACCCACCATGAC

AGGAAGAACGGCCGCAGCAGCTCTGGGGCCCTCCGTGGGGTCTGCTCCTGCGTGGAA
SEQ ID NO 53
G   GTGGGTCCTGTAAGTTGTGGTTCCCGGTGGCTGAGGGGAAGGAAGGCAGACCTG
 4438

←SEQ ID NO 28     SEQ ID NO 29→
GGCCTTTnn~800bp~nnGACAGAGTGCCATCTCTGCCTCCCAAAGCTCTAAGAG

CCATGTCCCAAGCCTATACCCCATCCCACAACTGCAGCCTCATCACTGTCCTGTCTT

CCAGC   CGGCAAAGCCTGCGACCCCGCAGCCAGGCAGTTCAACACCCTCATCCCCT
    4439

GGTGCCTGCCCCACACCGGGAACCGGCACAACCACTGGGCTGGCCTCTATGGAAGGC

TCGAGTGGGACGGCTTCTTCAGCACAACCGTCACCAACCCCGAGCCCATGGGCAAGC

AGG   TAGGTGGGGAGGGGGCATCCGAGGGCCTGGGTCAGGCTGTACTTGGCGGCCT
   4606
AACTAGGTGGAAGTGTGGGTTTAGCCAAGTGGGGACAGCACCCCAGGATCCCCCAG
←SEQ ID NO 29    SEQ ID NO 30→
GCACCTGnn~400bp~nnAGACTGCTCTGCCTCCTGCCCCTCCACGTCCACGGAC

AAGCTCATAGCCAAGCCATGGCCGTATGCTGTCACAGTGCCATTTCCCTCCCTGTCC

CCGACGGTGACCCGGCCTGGGTGCTACTGCCCTCGCCCACCGCGCCTCTTTCCCCCA
SEQ ID NO 54
GGG   CCGCGTGCTCCACCCAGAGCAGCACCGTGTGGTGAGCGTGCGGGAGTGTGCC
   4607

CGCTCCCAGGGCTTCCCTGACACCTACCGGCTCTTCGGCAACATCCTGGACAAGCAC
SEQ ID NO 55
CGGCAG   TCAGTGGGGCGGCGCGCTGGGTCTGGACAGGAAGGAGGCTTCTGTGCCT
    4722
                   ←SEQ ID NO 30         SEQ ID NO 31→
GTCACCAGGTGGGGCTGGGGCAGCGCAGTCACTTnn~1450bp~nnCAATGCCCA

GGTTGTCCTCCATCTGAGCAGGTGCTGGAGTACACCTCCCCGGCCTTGGGCCTGGT

GTCCACATCAGGCATTGCCCTTCTCCCCTCCTGCAGG   TGGGCAATGCCGTGCCAC
                                    4723

CGCCCCTGGCCAAAGCCATTGGCTTGGAGATCAAGCTTTGTATGTTGGCCAAAGCCC
         SEQ ID NO 56
GAGAGAGTGCC   GTATGGTGGGGTGGGCCAGGCTTCCTCTGGGGCCTGACTGCCCT
         4809
```

←SEQ ID NO 31   SEQ ID NO 32→
CTGGGGTACATGTGGGGGCAGnn~550bp~nnACTGAGCCTCTGGGTCTAGAACC

TCTGGGGACCGTTTGAGGAGTGTTCAGTCTCCGTGAACGTTCCCTTAGCACTCTGCC

ACTTATTGGGTCAGCTGTTAACATCAGTACGTTAATGTTTCCTGATGGTCCATGTCT

GTTACTCGCCTGTCAAGAGGCGTGACACCGGGCGTGTTCCCCAGAGTGACTTTTCCT

TTTATTTCCCTT$_{4810}$CAGCTAAAATAAAGGAGGAGGAAGCTGCTAAGGACTAGTTCTG

CCCTCCCGTCACCCCTGTTTCTGGCACCAGGAATCCCCAACATGCACTGATGTTGTG

TTTTTAACATGTCAATCTGTCCGTTCACATGTGTGGTACATGGTGTTTGTGGCCTTG

GCTGACATGAAGCTGTTGTGTGAGGTTCGCTTATCAACTAATGATTTAGTGATCAAA

TTGTGCAGTACTTTGTGCATTCTGGATTTTAAAAGTTTTTTATTATGCATTATATCA

AATCTACCACTGTATGAGTGGAAATTAAGACTTTATGTAGTTTTTATATGTTGTAAT

←SEQ ID NO 32
ATTTCTTCAAATAAATCTCTCCTATAAACCA$_{5169}$ 3'

FIG. 1J

OLIGONUCLEOTIDE: C U I

190kDa →

CONDITIONS:

OLIGONUCLEOTIDE: C U I

CONDITIONS: BOILED PRIOR TO PAGE

OLIGONUCLEOTIDE:  C   U   I

CONDITIONS: WESTERN BLOT REACTED
WITH AN αDNA MeTase
ANTISERA

US 6,020,318

DNA METHYLTRANSFERASE GENOMIC SEQUENCES AND ANTISENSE OLIGONUCLEOTIDES

BACKGROUND OF THE INVENTION

1. Field of the Invention

The invention relates to modulation of gene expression. In particular, the invention relates to modulation of gene expression of the gene encoding DNA methyltransferase, and to modulation of gene expression that is regulated by the enzyme DNA methyltransferase.

2. Summary of the Related Art

Modulation of gene expression has become an increasingly important approach to understanding various cellular processes and their underlying biochemical pathways. Such understanding enriches scientific knowledge and helps lead to new discoveries of how aberrancies in such pathways can lead to serious disease states. Ultimately, such discoveries can lead to the development of effective therapeutic treatments for these diseases.

One type of cellular process that is of particular interest is how the cell regulates the expression of its genes. Aberrant gene expression appears to be responsible for a wide variety of inherited genetic disorders, and has also been implicated in numerous cancers and other diseases. Regulation of gene expression is a complex process, and many aspects of this process remain to be understood. One of the mysteries of this process resides in the fact that while the genetic information is the same in all tissues that constitute a multicellular organism, the expression of functions encoded by the genome varies significantly in different tissues.

In some cases, tissue-specific transcription factors are known to play a role in this phenomenon. (See Maniatis et al., Science 236: 1237–1245 (1987); Ingarham et al., Annual Review of Physiology 52: 773–791 (1990). However, several important cases exist that cannot be readily explained by the action of transcription factors alone. For example, Midgeon, Trends Genet. 10: 230–235 (1994), teaches that X-inactivation involves the inactivation of an allele of a gene that resides on the inactive X-chromosome, while the allele on the active X-chromosome continues to be expressed. In addition, Peterson and Sapienza, Annu. Rev. Genet. 27: 7–31 (1993), describes "parental imprinting", where an allele of a gene that is inherited from one parent is active and the other allele inherited from the other parent is inactive. In both of these cases, both alleles exist in an environment containing the same transcription factors, yet one allele is expressed and the other is silent. Thus, something other than transcription factors must be involved in these phenomena.

Investigators have been probing what type of "epigenetic information" may be involved in this additional control of the expression pattern of the genome. Holliday, Philos. Trans. R. Soc. Lond. B. Biol. Sci. 326: 329–338 (1990) discusses the possible role for DNA methylation in such epigenetic inheritance. DNA contains a set of modifications that is not encoded in the genetic sequence, but is added covalently to DNA using a different enzymatic machinery. These modifications take the form of methylation at the 5 position of cytosine bases in CpG dinucleotides. Numerous studies have suggested that such methylation may well be involved in regulating gene expression, but its precise role has remained elusive. For example, Lock et al., Cell 48: 39–46 (1987), raises questions about whether the timing of hypermethylation and X-inactivation is consistent with a causal role for methylation. Similarly, Bartolomei et al., Genes Dev. 7: 1663–1673 (1993) and Brandeis et al., EMBO J. 12: 3669–3677 (1993), disclose timing/causation questions for the role of methylation in parental imprinting.

Some of the shortcomings of existing studies of the role of DNA methylation in gene expression reside in the tools that are currently available for conducting the studies. Many studies have employed 5-azaC to inhibit DNA methylation. However, 5-azaC is a nucleoside analog that has multiple effects on cellular mechanisms other than DNA methylation, thus making it difficult to interpret data obtained from these studies. Similarly, 5-azadC forms a mechanism based inhibitor upon integration into DNA, but it can cause trapping of DNA methyltransferase (hereinafter, DNA MeTase) molecules on the DNA, resulting in toxicities that may obscure data interpretation.

More recently, Szyf et al., J. Biol. Chem. 267: 12831–12836 (1995), discloses a more promising approach using expression of antisense RNA complementary to the DNA MeTase gene to study the effect of methylation on cancer cells. Szyf and von Hofe, U.S. Pat. No. 5,578,716, discloses the use of antisense oligonucleotides complementary to the DNA MeTase gene to inhibit tumorigenicity. These developments have provided powerful new tools for probing the role of methylation in numerous cellular processes. In addition, they have provided promising new approaches for developing therapeutic compounds that can modulate DNA methylation. One limitation to these approaches is that their effect is not immediate, due to the half life of DNA MeTase enzyme. Thus, although the expression of DNA MeTase is modulated, residual DNA MeTase enzyme can continue to methylate DNA until such residual enzyme is degraded. Polysome-associated DNA MeTase mRNA may also persist for some time, allowing additional translation to produce additional DNA MeTase enzyme. There is, therefore, a need for new antisense oligonucleotides which can act against intron regions of DNA MeTase RNA in the nucleus before its processing and association with polysomes. The development of such oligonucleotides will require obtaining sequence information about the non-coding regions of DNA MeTase RNA.

BRIEF SUMMARY OF THE INVENTION

The invention provides recombinant nucleic acids comprising nucleic acid sequences from the genomic DNA methyltransferase gene (DNA MeTase). The invention also provides recombinant nucleic acids comprising nucleic acid sequences complementary to the genomic DNA MeTase gene. The invention further provides sequence information for such nucleic acid sequences. In addition, the invention provides antisense oligonucleotides complementary to special target regions of the genomic DNA MeTase gene or its RNA transcript. Finally, the invention provides methods for using such antisense oligonucleotides as analytical and diagnostic tools, as potentiators of transgenic plant and animal studies and for gene therapy approaches, and as potential therapeutic agents.

In a first aspect, the invention provides novel recombinant nucleic acid sequences comprising at least one nucleotide sequence selected from the nucleotide sequences of the genomic DNA MeTase gene. The sequence of the sense strand of the genomic DNA MeTase gene is shown in FIG. 1. The nucleotide sequence of the sense strand of the DNA MeTase gene is also set forth in the Sequence Listings as SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, and SEQ ID NO 32.

In a second aspect, the invention provides novel recombinant nucleic acid sequences complementary to at least one nucleotide sequence selected from the nucleotide sequences set forth in the Sequence Listings as SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, and SEQ ID NO 32.

In a third aspect, the invention provides antisense oligonucleotides which inhibit the expression of DNA MeTase. Such antisense oligonucleotides are complementary to a special target region of RNA or double-stranded DNA that encodes DNA MeTase. Preferably, such antisense oligonucleotides contain one or more modified internucleoside linkage and may optionally contain either deoxyribonucleosides, ribonucleosides or 2'-O-substituted ribonucleosides, or any combination thereof. Particularly preferred antisense oligonucleotides according to this aspect of the invention include chimeric oligonucleotides and hybrid oligonucleotides.

In a fourth aspect, the invention provides a method for investigating the role of DNA MeTase in cellular growth, including the growth of tumor cells. In the method according to this aspect of the invention, the cell type of interest is contacted with an antisense oligonucleotide according to the invention, resulting in inhibition of expression of DNA MeTase in the cell. The antisense oligonucleotides can be administered at different points in the cell cycle, or in conjunction with promoters or inhibitors of cell growth to determine the role of DNA MeTase in the growth of the cell type of interest.

In a fifth aspect, the invention provides methods for inhibiting tumor growth comprising administering to a mammal, including a human, antisense oligonucleotides according to the invention. In the method according to this aspect of the invention a therapeutically effective amount of an antisense oligonucleotide according to the invention is administered for a therapeutically effective period of time to a mammal, including a human, which has tumor cells present in its body.

BRIEF DESCRIPTION OF THE DRAWINGS

FIGS. 1A–1J shows the nucleotide sequence for the sense strand of the DNA MeTase gene comprising the nucleotide acid sequences set forth in the Sequence Listings as SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, and SEQ ID NO 32. Nucleotides in coding regions are identified as bold characters. Subscript numbers correspond to the DNA MeTase cDNA numbering of Yen et al. (Nucleic Acids Res. 9: 2287–2291 (1992)). Preferred special target regions are underlined.

DETAILED DESCRIPTION OF THE PREFERRED EMBODIMENTS

Figure 2A:
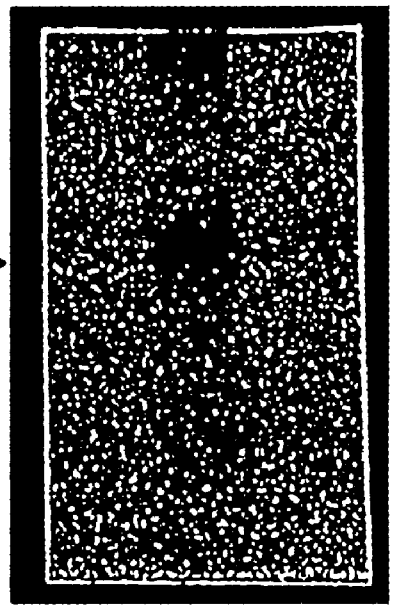
FIGS. 2A–2D are representations of autoradiographs (panels A, B and D) and Western blots (panel C) in an experiment to identify complex formation between the oligonucleotides of the invention and DNA MeTase enzyme. Complex formation was reversed by boiling, and was independent of SAM.
Figure 2B:
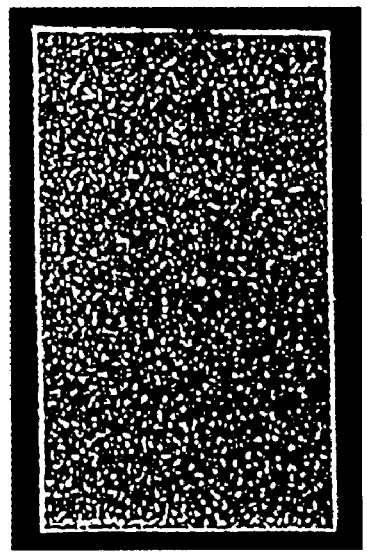
Figure 2C:
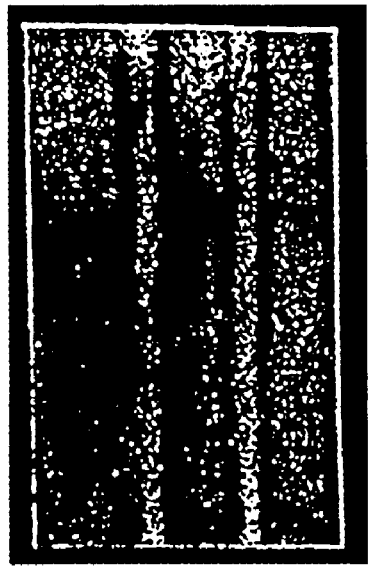
Figure 2D:
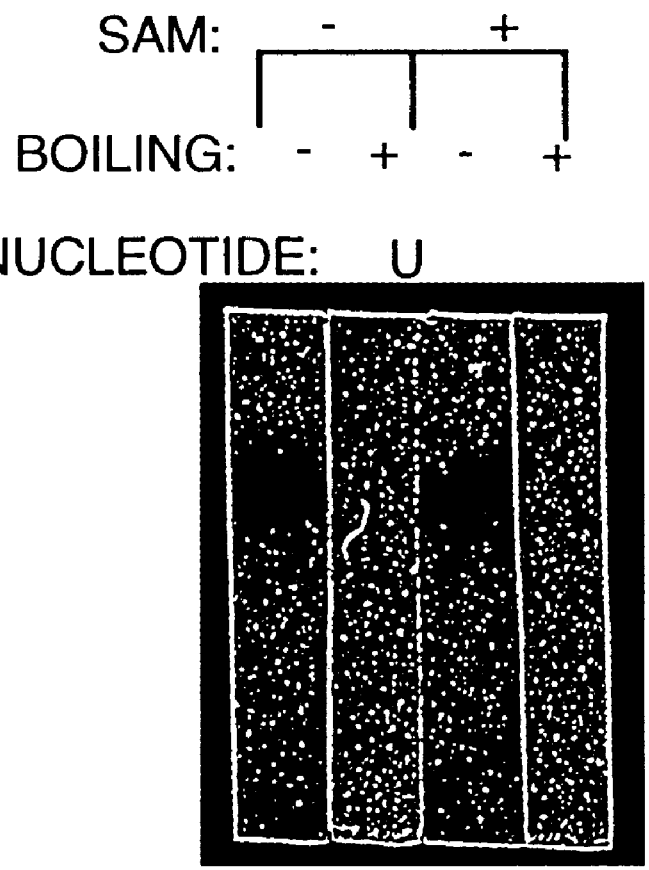

The invention relates to modulation of gene expression. In particular, the invention relates to modulation of gene expression of the gene encoding DNA methyltransferase (DNA MeTase), and to modulation of gene expression that is regulated by the enzyme DNA MeTase. The patents and publications identified in this specification are within the knowledge of those skilled in this field and are hereby incorporated by reference in their entirety.

The invention provides recombinant nucleic acids comprising nucleic acid sequences from the genomic DNA MeTase gene. The invention further provides sequence information for such nucleic acid sequences. In addition, the invention provides antisense oligonucleotides complementary to regions of the genomic DNA MeTase gene or its RNA transcript which could not be targeted in the absence of such information. Finally, the invention provides methods for using such antisense oligonucleotides as analytical and diagnostic tools, as potentiators of transgenic plant and animal studies and gene therapy approaches, and as potential therapeutic agents.

In a first aspect, the invention provides novel recombinant nucleic acid sequences comprising at least one nucleotide sequence selected from the nucleotide sequences of the genomic DNA MeTase gene. The sequence of the sense strand of the genomic DNA MeTase is shown in FIG. 1. Coding regions are identified as bold sequences.

In one preferred embodiment, the recombinant DNA molecule according to the invention comprises at least one nucleotide sequences selected from the nucleotide sequences shown in FIG. 1 and corresponding to Sequence Listings SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, and SEQ ID NO 32, in a replicatable vector. As used herein, the term "replicatable vector" designates a nucleic acid vector able to replicate in at least one cell type. Many such replicatable vectors are well known in the art (see e.g., Molecular Cloning, 2d Edition, Cold Spring Harbor Laboratory Press (1989)).

In an additional preferred embodiment, the recombinant DNA molecule according to the invention comprises nucleotide sequences complementary to at least a portion of the nucleotide sequence shown in FIG. 1, and corresponding to at least one of the nucleotide sequences set forth as Sequence Listings SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18 SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, and SEQ ID NO 32, in a replicatable vector.

In another preferred embodiment, the replicatable vector is an expression vector. The term "expression vector" refers, in one embodiment, to a replicatable vector able to support the translation of part or all of its sequences into one or more peptides. The expression vector of this invention may replicate autonomously in the host cell, or may become integrated into the host cell DNA. The expression vector can be used to transform a host cell which is capable of expressing the nucleotide sequence shown in FIG. 1.

In yet another preferred embodiment, the term expression vector refers to a vector capable of supporting the transcription of part or all of its sequences into one or more transcripts. The vector according to this embodiment of the invention may replicate autonomously in the host cell, or may become integrated into the host cell DNA. The vector can be used to transform a host cell which is capable of transcription of the nucleotide sequence complementary to the nucleotide sequence shown in FIG. 1. Preparation of recombinant DNA molecules and expression vectors and their use to transform host cells is well known in the art (see e.g., Molecular Cloning, 2d Edition, Cold Spring Harbor Laboratory Press (1989)).

In yet another embodiment, the invention also provides a host cell comprising recombinant DNA molecules according to the invention. According to this invention the term "host cell" refers to a cell which expresses the nucleotide sequences according to this invention.

This first aspect of the invention further provides a method for preparing DNA MeTase enzyme or a fragment thereof. The method according to this aspect of the invention comprises culturing a host cell in an appropriate culture media to express the nucleotide sequences according to the invention. Consequently, the host cell of the invention produces DNA MeTase enzyme or a fragment thereof, which may be conveniently separated from the host cell and the culture media by affinity binding, as described in detail in this specification. Fragments of DNA MeTase enzyme can then be used to produce antibodies specific for epitopes of DNA MeTase enzyme, according to standard immunological procedures. Such antibodies can be used to purify DNA MeTase enzyme, or to quantify it in conventional immunological assays.

In a second aspect, the invention provides a novel recombinant nucleic acid molecule comprising nucleic acid sequences complementary to at least part of the genomic DNA MeTase gene. The sequence of the sense strand of the genomic DNA MeTase is shown in FIG. 1. Coding regions are identified as bold sequences. For purposes of the invention, "complementary" means being sufficiently complementary to have the ability to hybridize to a genomic region, a gene, or an RNA transcript thereof under physiological conditions. Such hybridization is ordinarily the result of base-specific hydrogen bonding between complementary strands, preferably to form Watson-Crick or Hoogsteen base pairs, although other modes of hydrogen bonding, as well as base stacking can also lead to hybridization. As a practical matter, such complementarity can be inferred from the observation of specific DNA MeTase gene expression inhibition.

In one preferred embodiment, the recombinant DNA molecule according to the invention comprises nucleotide acid having a sequence complementary to at least part of the nucleotide sequences shown in FIG. 1, and complementary to at least one of the nucleotide sequences set forth in the Sequence Listings as SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, and SEQ ID NO 32, in a replicatable vector. In another preferred embodiment the replicatable vector is an expression vector. The replicatable vectors and expression vectors appropriate for this aspect of the invention are generally the same well known materials as discussed for the first aspect of the invention.

In yet another embodiment, the invention provides a host cell comprising recombinant DNA molecules according to the invention. This second aspect of the invention further provides a method for inhibiting DNA MeTase enzyme expression in a transfected cell or transgenic animal. The method according to this aspect of the invention comprises culturing a host cell in an appropriate culture media to express the nucleotide sequences according to this aspect of the invention. Consequently, the host cell of the invention produces decreased levels of DNA MeTase enzyme.

In a third aspect, the invention provides antisense oligonucleotides which inhibit the expression of DNA MeTase. Such antisense oligonucleotides are complementary to a special target region of RNA or double-stranded DNA that encodes DNA MeTase.

The term "special target region" is used to denote sequences which could not be targeted without the sequence information provided by the invention. In particular, such special target regions comprise a portion of the non-coding region of the nucleic acid shown in FIG. 1. Most preferably, such special target region comprises from about 2 to about 50 nucleotides of such noncoding sequences. Such special target regions include, without limitation, intronic sequences, untranslated 5' and 3' regions as well as intron-exon boundaries from the DNA methyltransferase gene. In certain embodiments, said target region may further comprise coding regions from the DNA MeTase gene.

Preferred non-limiting examples of antisense oligonucleotides complementary to special target regions of RNA or double-stranded DNA encoding DNA MeTase according to the invention are shown in Table 1. Additional preferred oligonucleotides complementary to such special target regions have nucleotide sequences of from about 21 to about 35 nucleotides which include the nucleotide sequences shown in Table 1. Yet additional preferred oligonucleotides complementary to such special target regions have nucleotide sequences of from about 13 to about 19 nucleotides of the nucleotide sequences shown in Table 1.

TABLE 1

| SEQ. ID NO. | SEQUENCE | TARGET (*) |
|---|---|---|
| 33 | 5' AGA ACT GAC TTA CCT CGG AT 3' | 216 |
| 34 | 5' AGG GTG GGT CTG TGG GAG CA 3' | 1037 |
| 35 | 5' CAG TAC ACA CTA GAC AGG AA 3' | 1220 |
| 36 | 5' CAC ACT TAC AGG TGC TGA AG 3' | 1441 |
| 37 | 5' GAT CTC TTA CCT CGA TCT TG 3' | 1593 |
| 38 | 5' CGC ATC CTT ACC TCT GTC CC 3' | 1782 |
| 39 | 5' GGT GAG GTT ACC TCA CAG AC 3' | 1970 |
| 40 | 5' GGC CTG ACC TAC CTC CGC TC 3' | 2069 |
| 41 | 5' CCA AGG GTT ACC TTG ACG GC 3' | 2214 |
| 42 | 5' AAA GAT GCA AAC CTT GCT AG 3' | 2332 |
| 43 | 5' TCC ATG CCT CCC TTG GGT AG 3' | 2537 |
| 44 | 5' CCA GTG CTC ACT TGA ACT TG 3' | 2669 |
| 45 | 5' ACA CAG AAT CTG AAG GAA AC 3' | 2670 |
| 46 | 5' AGC TTG ATG CTG CAG AGA AG 3' | 2844 |
| 47 | 5' ACG GGG CAC CAC CTC GAG GA 3' | 3259 |
| 48 | 5' CTT GCC CTT CCC TGG GGG AG 3' | 3345 |
| 49 | 5' ACG GCC GCT CAC CTG CTT GG 3' | 3473 |
| 50 | 5' TCC CGG CCT GTG GGG GAG AA 3' | 3898 |
| 51 | 5' GGG CCA CCT ACC TGG TTA TG 3' | 4066 |
| 52 | 5' GGG TGC CAT TAC CTT ACA GA 3' | 4241 |
| 53 | 5' ACA GGA CCC ACC TTC CAC GC 3' | 4438 |
| 54 | 5' GCA CGC GGC CCT GGG GGA AA 3' | 4607 |
| 55 | 5' GCC CCA CTG ACT GCC GGT GC 3' | 4719 |
| 56 | 5' CCC GGG TGG TAT GCC GTG AG 3' | 4810 |
| 57 | 5' CTG CTC TTA CGC TTA GCC TC 3' | 442 |
| 58 | 5' GAA GGT TCA GCT GTT TAA AG 3' | 443 |
| 59 | 5' GTT TGG CAG GGC TGT CAC AC 3' | 518 |
| 60 | 5' CTG GCC CTA CCT GGT CTT TG 3' | 597 |
| 61 | 5' CTA GCA ACT CTG TCA AGC AA 3' | 632 |
| 62 | 5' TAG AGC TTT ACT TTT TCA TC 3' | 718 |
| 63 | 5' GTT TGG GTG TTC TGT CAC AG 3' | 753 |
| 64 | 5' GTT TGG CAG CTC TGC AGG GT 3' | 876 |

For purposes of the invention, the term "oligonucleotide" includes polymers of two or more deoxyribonucleosides, ribonucleosides, or 2'-O-substituted ribonucleoside residues, or any combination thereof. Preferably, such oligonucleotides have from about 8 to about 50 nucleoside residues, and most preferably from about 12 to about 30 nucleoside residues. The nucleoside residues may be coupled to each other by any of the numerous known internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleotide linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane. For purposes of the invention the term "2'—O-substituted" means substitution of the 2' position of the pentose moiety with an —O-lower alkyl group containing 1–6 saturated or unsaturated carbon atoms, or with an —O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group.

Particularly preferred antisense oligonucleotides according to this aspect of the invention include chimeric oligonucleotides and hybrid oligonucleotides.

For purposes of the invention, a "chimeric oligonucleotide" refers to an oligonucleotide having more than one type of internucleoside linkage. One preferred embodiment of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region. Preferably, such chimeric oligonucleotides contain at least three consecutive internucleoside linkages selected from phosphodiester and phosphorothioate linkages, or combinations thereof.

For purposes of the invention, a "hybrid oligonucleotide" refers to an oligonucleotide having more than one type of nucleoside. One preferred embodiment of such a hybrid oligonucleotide comprises a ribonucleotide or 2'-O-substituted ribonucleotide region, preferably comprising from about 2 to about 12 2'-O-substituted nucleotides, and a deoxyribonucleotide region. Preferably, such a hybrid oligonucleotide will contain at least three consecutive deoxyribonucleosides and will also contain ribonucleosides, 2'-O-substituted ribonucleosides, or combinations thereof.

The exact nucleotide sequence and chemical structure of an antisense oligonucleotide according to the invention can be varied, so long as the oligonucleotide retains its ability to inhibit DNA MeTase expression. This is readily determined by testing whether the particular antisense oligonucleotide is active in a DNA MeTase enzyme assay, a soft agar growth assay, or an in vivo tumor growth assay, all of which are described in detail in this specification.

Antisense oligonucleotides according to the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG). (See, e.g., Pon, Methods in Molec. Biol. 20: 465 (1993)).

Antisense oligonucleotides according to the invention are useful for a variety of purposes. For example, they can be used as "probes" of the physiological function of DNA MeTase by being used to inhibit the activity of DNA methyltransferase in an experimental cell culture or animal system and to evaluate the effect of inhibiting such DNA MeTase activity. This is accomplished by administering to a cell or an animal an antisense oligonucleotide according to the invention and observing any phenotypic effects. In this use, antisense oligonucleotides according to the invention are preferable to traditional "gene knockout" approaches because they are easier to use and can be used to inhibit DNA MeTase activity at selected stages of development or differentiation. Thus, antisense oligonucleotides according to the invention can serve as probes to test the role of DNA methylation in various stages of development.

Finally, antisense oligonucleotides according to the invention are useful in therapeutic approaches to benign and malignant tumors and other human diseases involving suppression of gene expression. The anti-tumor utility of antisense oligonucleotides according to the invention is described in detail elsewhere in this specification. In addition, antisense oligonucleotides according to the invention may be used to activate silenced genes to provide a missing gene function and thus ameliorate disease symptoms. For example, the diseases beta thalassemia and sickle cell anemia are caused by aberrant expression of the adult beta globin gene. Most individuals suffering from these diseases have normal copies of the fetal gene for beta globin. However, the fetal gene is hypermethylated and is silent. Activation of the fetal globin gene could provide the needed globin function, thus ameliorating the disease symptoms.

For therapeutic use, antisense oligonucleotides according to the invention may optionally be formulated with any of the well known pharmaceutically acceptable carriers or diluents. This formulation may further contain one or more DNA MeTase inhibitor and/or one or more additional anti-DNA MeTase antisense oligonucleotide or it may contain any other pharmacologically active agent.

In a fourth aspect, the invention provides a method for investigating the role of DNA MeTase in cellular growth, including the growth of tumor cells. In the method according to this aspect of the invention, the cell type of interest is contacted with an antisense oligonucleotide according to the invention, resulting in inhibition of expression of DNA MeTase in the cell. The antisense oligonucleotides can be administered at different points in the cell cycle, or in conjunction with promoters or inhibitors of cell growth to determine the role of DNA MeTase in the growth of the cell type of interest.

In a fifth aspect, the invention provides methods for inhibiting tumor growth comprising administering to an animal, including a human, antisense oligonucleotides according to the invention. In the method according to this aspect of the invention a therapeutically effective amount of an antisense oligonucleotide according to the invention is administered for a therapeutically effective period of time to an animal, including a human, which has at least one tumor cell present in its body.

As used herein the term "tumor growth" is used to refer to the growth of a tumor cell. A "tumor cell" is a neoplastic cell. A tumor cell may be benign, i.e. one that does not form metastases and does not invade and destroy adjacent normal tissue, or malignant, i.e. one that invades surrounding tissues, is capable of producing metastases, may recur after attempted removal, and is likely to cause death of the host.

The terms "therapeutically effective amount" and "therapeutically effective period of time" are used to denote known treatments at dosages and for periods of time effective to reduce tumor cell growth. Preferably, such administration should be parenteral, oral, sublingual, transdermal, topical, intranasal or intrarectal. When administered systemically, the therapeutic composition is preferably administered at a sufficient dosage to attain a blood level of antisense oligonucleotide from about 0.01 $\mu$M to about 10 $\mu$M. For localized administration, much lower concentrations than this may be effective, and much higher concentrations may be tolerated. Preferably, a total dosage of DNA MeTase inhibitor will range from about 0.1 mg oligonucleotide per patient per day to about 200 mg oligonucleotide per kg body weight per day.

According to another embodiment, one or more of the oligonucleotides of the invention may be administered to an animal this aspect of the invention provides methods for inhibiting tumor growth comprising administering to an animal, including a human, more than one antisense oligonucleotide according to the invention either sequentially or simultaneously in a therapeutically effective amount and for a therapeutically effective period of time.

The following examples are intended to further illustrate certain preferred embodiments of the invention and are not limiting in nature.

EXAMPLE 1

Inhibition of DNA MeTase Expression as Measured in Nuclear Extracts Prepared from Human or Murine Cells Nuclear extracts are prepared from $1 \times 10^8$ mid-log phase human H446 cells or mouse Y1 cells which have been grown under standard cell culture conditions. Cells were treated with medium supplemented with 1 mg/ml of an antisense oligonucleotide complementary to a noncoding region of the DNA MeTase RNA transcript or a randomer (negative control) oligonucleotide. The cells are harvested and washed twice with phosphate buffered saline (PBS), then the cell pellet is resuspended in 0.5 ml Buffer A (10 mM Tris pH 8.0, 1.5 mM $MgCl_2$, 5 mM $KCl_2$, 0.5 mM DTT, 0.5 mM PMSF and 0.5% Nonidet P40) to separate the nuclei from other cell components. The nuclei are pelleted by centrifugation in an Eppendorf microfuge at 2,000 RPM for 15 min at 4° C. The nuclei are washed once in Buffer A and re-pelleted, then resuspended in 0.5 ml Buffer B (20 mM Tris pH 8.0, 0.25% glycerol, 1.5 mM $MgCl_2$, 0.5 mM PMSF, 0.2 mM EDTA 0.5 mM DTT and 0.4 mM NaCl). The resuspended nuclei are incubated on ice for 15 minutes then spun at 15,000 RPM to pellet nuclear debris. The nuclear extract in the supernatant is separated from the pellet and used for assays for DNA MeTase activity. For each assay, carried out in triplicate, 3 $\mu$g of nuclear extract is used in a reaction mixture containing 0.1 $\mu$g of a synthetic 33-base pair hemimethylated DNA molecule substrate with 0.5 $\mu$Ci S-[methyl-$^3$H] adenosyl-L-methionine (78.9 Ci/mmol) as the methyl donor in a buffer containing 20 mM Tris-HCl (pH 7.4), 10 mM EDTA, 25% glycerol, 0.2 mM PMSF, and 20 mM 2-mercaptoethanol. The reaction mixture is incubated for 1 hour at 37° C. to measure the initial rate of the DNA MeTase. The reaction is stopped by adding 10% TCA to precipitate the DNA, then the samples are incubated at 4° C. for 1 hour and the TCA precipitates are washed through GFC filters (Fischer, Hampton, N.H.). Controls are DNA incubated in the reaction mixture in the absence of nuclear extract, and nuclear extract incubated in the reaction mixture in the absence of DNA. The filters are laid in scintillation vials containing 5 ml of scintillation cocktail and tritiated methyl groups incorporated into the DNA are counted in a β-scintillation counter according to standard methods. To measure inhibition of DNA MeTase expression, the specific activity of the nuclear extract from oligonucleotide-treated cells is compared with the specific activity of the extract from untreated cells. Treatment of cells with antisense oligonucleotides of the invention results in reduction in DNA MeTase activity in the nuclear extract.

EXAMPLE 2

Antisense Oligonucleotide Accumulation in Cells

Antisense oligonucleotides are labeled with $^{32}$p using standard procedures. 300,000 Y1 cells per well are plated in a six-well tissue culture plate. Labeled antisense oligonucleotides are added to a final concentration of 1 μM. Cells are harvested at different time points by trypsinization according to methods well known in the art, and washed extensively with PBS to remove nonincorporated compounds. The cell pellet is resuspended in 20 μl buffer RIPA (0.5% deoxycholic acid, 0.1% SDS, 1% NP-40, in PBS). The homogenate is incubated at 4° C. for 30 minutes, then spun in a microfuge at maximum speed for 30 minutes, after which the supernatant is transferred to a new tube. Two μl of supernatant are extracted with phenol-chloroform by adding 1 μl of phenol and 1 μl of chloroform, the suspension is mixed and the organic and aqueous phases are separated by centrifugation in a microfuge for 10 minutes at 15,000 RPM. The aqueous phase is extracted and loaded onto a 20% polyacrylamide-urea gel. Visualization is by autoradiography. The results demonstrate that antisense oligonucleotides are taken up by the cells in a time-dependent manner.

EXAMPLE 3

Analysis of Cellular DNA Methylation in Cells Treated with Antisense Oligonucleotides Nuclear extracts are prepared from randomer oligonucleotide-treated cells and from antisense oligonucleotide-treated cells (1 μM oligonucleotide) as described in Example 1. The DNA pellet is resuspended in 0.5 ml DNA extraction buffer (0.15 M NaCl, 1% SDS, 20 mM Tris-HCl pH 8.0, 5 mM EDTA), 100 μg Proteinase K is added, and the suspension is incubated at 50° C. for 16 hours. The DNA is extracted in phenol-chloroform by adding 0.25 ml phenol and 0.25 ml chloroform. The suspension is mixed and the organic and aqueous phases are separated by centrifugation in a microfuge for 10 minutes at 15,000 RPM. One ml absolute ethanol is added to the aqueous phase and the DNA is precipitated by centrifugation in a microfuge for 15 minutes at 15,000 RPM. The DNA pellet is washed in 70% ethanol and re-pelleted by centrifugation. The DNA is resuspended in 100 μl 20 mM Tris-HCl pH 8.0, 1 mM EDTA.

Two μg DNA are incubated at 37° C. for 15 minutes with 0.1 unit of DNase, 2.5 μl $^{32}$P-α-dGTP (3000 Ci/mmol, Amersham, (Cleveland, Ohio) and then 2 units Kornberg DNA Polymerase (Boehringer Mannheim, Mannheim, Germany) are added and the reaction mixture is incubated for an additional 25 minutes at 30° C. Fifty μl H$_2$O are then added and nonincorporated radioactivity is removed by spinning through a Microspin S-300 HR column (Pharmacia, Piscataway, N.J.). Labelled DNA (20 μl) is digested with 70 μg micrococcal nuclease (Pharmacia, Piscataway, N.J.) in the manufacturer's recommended buffer for 10 hours at 37° C. Equal amounts of radioactivity are loaded onto TLC phosphocellulose plates (Merck, Darmstadt, Germany) and the 3' mononucleotides are separated by chromatography in one direction, in 66:33:1 isobutyric acid/H$_2$O/NH$_4$OH. The chromatograms are exposed to XAR film (Eastman Kodak, Rochester, N.Y.) and the autoradiograms are scanned by laser densitometry (Scanalytics, CSPI, Billerica, Mass.). Spots corresponding to cytosine and 5-methylcytosine are quantified and the percentage of non-methylated CG dinucleotides is determined. The results are expected to demonstrate an overall reduction in the percentage of non-methylated CG dinucleotides in antisense oligonucleotide-treated cells, relative to randomer-treated cells.

To assess demethylation of specific genes, a procedure is carried out as generally described in J. Biol. Chem. 270: 12690–12696 (1995). Briefly, the genomic DNA (10 μg) is extracted and subjected to digestion by 25 units HindIII, followed by digestion by either 25 units MspI (CG methylation insensitive) or 25 units HpaII (CG methylation sensitive) for 8 hours at 37° C. The digested DNA is separated on a 1.5% agarose gel and subjected to Southern blotting and hybridization with specific probes. The results are expected to show that genes which are ordinarily heavily methylated in the test cells become undermethylated, whereas the methylation levels for genes which are not ordinarily heavily methylated in the test cells are not significantly affected.

EXAMPLE 4

Inhibition of Tumor Growth By Antisense Oligonucleotides

Y1 or H446 cells are plated on a 6 well plate at a density of 80,000 cells/well. Antisense oligonucleotide phosphorothioates complementary to a DNA MeTase noncoding region (about 0.5 to 20 μM) are added to the cells. The cells are similarly treated daily for 7 days. Then, the cells are harvested and 3,000 live cells are plated in soft agar, for example, as described in Freedman and Shin, Cell 3: 355–359 (1974). Two weeks after plating, the number of colonies formed in soft agar are scored by visual examination. In the case of active antisense oligonucleotides, a dose-dependent reduction in the number of colonies is observed.

Alternatively, 6 to 8 week old LAF-1 mice (Jackson Labs, Bar Harbor, Me.) are injected subcutaneously in the flank area with 2×10$^6$ Y1 cells. Three days later, the mice are injected with 1–5 mg/kg antisense oligonucleotide phosphorothioates complementary to a DNA MeTase noncoding region. This dosing is repeated every two days. After one month, the mice are sacrificed and the tumor size is determined according to standard protocols. (see e.g., Ramchandani et al. Proc. Natl. Acad. SCI. USA 94: 684–689 (1997) In the case of active antisense oligonucleotides, significant reduction in tumor size is observed, relative to controls treated with a randomized or a reverse antisense sequence.

EXAMPLE 5

Affinity Binding of DNA MeTase Enzyme

To demonstrate affinity binding of DNA MeTase enzyme, a binding substrate hairpin oligonucleotide having the sequence 5'-CTGAAmCGGATmCGTTTCGATCUGTTCAG-3' was provided at 4 μM concentration. The hairpin oligonucleotide was labeled using polynucleotide kinase and gamma $^{32}$P-γ-ATP (300 mCi/mmol, 50 μCi) (New England Biolabs, Beverly, Mass.) as recommended by the manufacturer. Labeled oligonucleotide was separated from nonincorporated radioactivity by passing through a G-50 Sephadex spin column (Pharmacia, Uppsala, Sweden). Labeled hairpin oligonucleotide (500 nM) was incubated with 5 μg nuclear extract prepared as described in Example 1. The incubation, in the same buffer used for the DNA MeTase activity assay, was at 37° C. for 30 minutes. To determine whether complex formation was dependent on the cofactor SAM, the reaction was carried out both in the presence and the absence of SAM). Then, loading dye (0.3 M Tris-HCl pH 8.8, 0.2% SDS, 10% glycerol, 28 mM 2-mercaptoethanol and 24 μg/ml bromophenol blue) was added and the sample was separated on a 5% SDS-polyacrylamide gel (SDS-PAGE) with a 4% stacking gel according to standard procedures. Following SDS-PAGE separation, the gel was exposed to autoradiography for visualization of a complex migrating at 190 kDa. Alternatively, the gel was electrotransferred onto a PVDF membrane (Amersham Life Sciences, Buckinghamshire, England) using a electrotransfer apparatus (BioRad, Hercules, Calif.) at 250 milliamperes for 2.5 hours in electrotransfer buffer (3.03 g/l Tris base, 14.4 g/l glycine, 1 g/l SDS, pH 8.3) for Western blotting with a DNA MeTase-specific antisera. The membrane was blocked for 1 hour in a buffer containing 5 mM Tris base, 200 mM NaCl, 0.5% Tween-20 and 5% dry milk. Rabbit antisera was raised according to standard procedures (see e.g., *Molecular Cloning*, 2d Edition, Cold Spring Harbor Laboratory Press (1989)) against a peptide sequence found in the catalytic domain of human and murine DNA MeTase (amino acids GQRLPQKGDVEMLKGGPPC). The antisera was added to the membrane at a 1:200 dilution and incubated for 1 hour. The membrane was washed with the blocking buffer, then reacted with a 1:5000 dilution of goat anti-rabbit secondary antibody (Amersham, Cleveland, Ohio) for an additional hour. The membrane was then washed for 10 minutes in blocking buffer, three times, and bands reacting with anti-DNA MeTase antibody were visualized using an ECL detection kit according to the manufacturer protocols (Amersham, Cleveland, Ohio).

The results demonstrated that a 190 kDa complex is detected by both autoradiography and Western blotting (see FIG. 2), strongly indicating that the 190 kDa complex is formed between the hairpin oligonucleotide and DNA MeTase enzyme. Subsequent experiments using antisera raised against another peptide sequence found in the catalytic domain of human and murine DNA MeTase (amino acids GGPPCQGFSGMNRFNSRTY (see, Ramchandani et al. supra) confirmed the same results. These results further demonstrated that such complex formation is independent of the cofactor SAM since none was present. Furthermore, data showed that complex formation is achieved within 30 minutes, thus suggesting that such complex formation provides an assay for the level of DNA MeTase in different cell samples and a method to purify methyltransferase by affinity binding.

EXAMPLE 6

Analysis of Treated Cells

Enzymatic activity profiles were performed to quantitate the ability of the synthetic oligonucleotides of the present invention to inhibit DNA methyltransferase expression. A549 cells (ATCC), and T24 cells (ATCC) were grown according to standard cell culture techniques. Cells were then treated for 24 hours with growth medium containing 250 nM of an antisense oligonucleotide complementary to a special target region of the DNA MeTase RNA transcript or a scrambled (negative control) oligonucleotide, and 10 μg/ml lipofectin.

Figure 3:
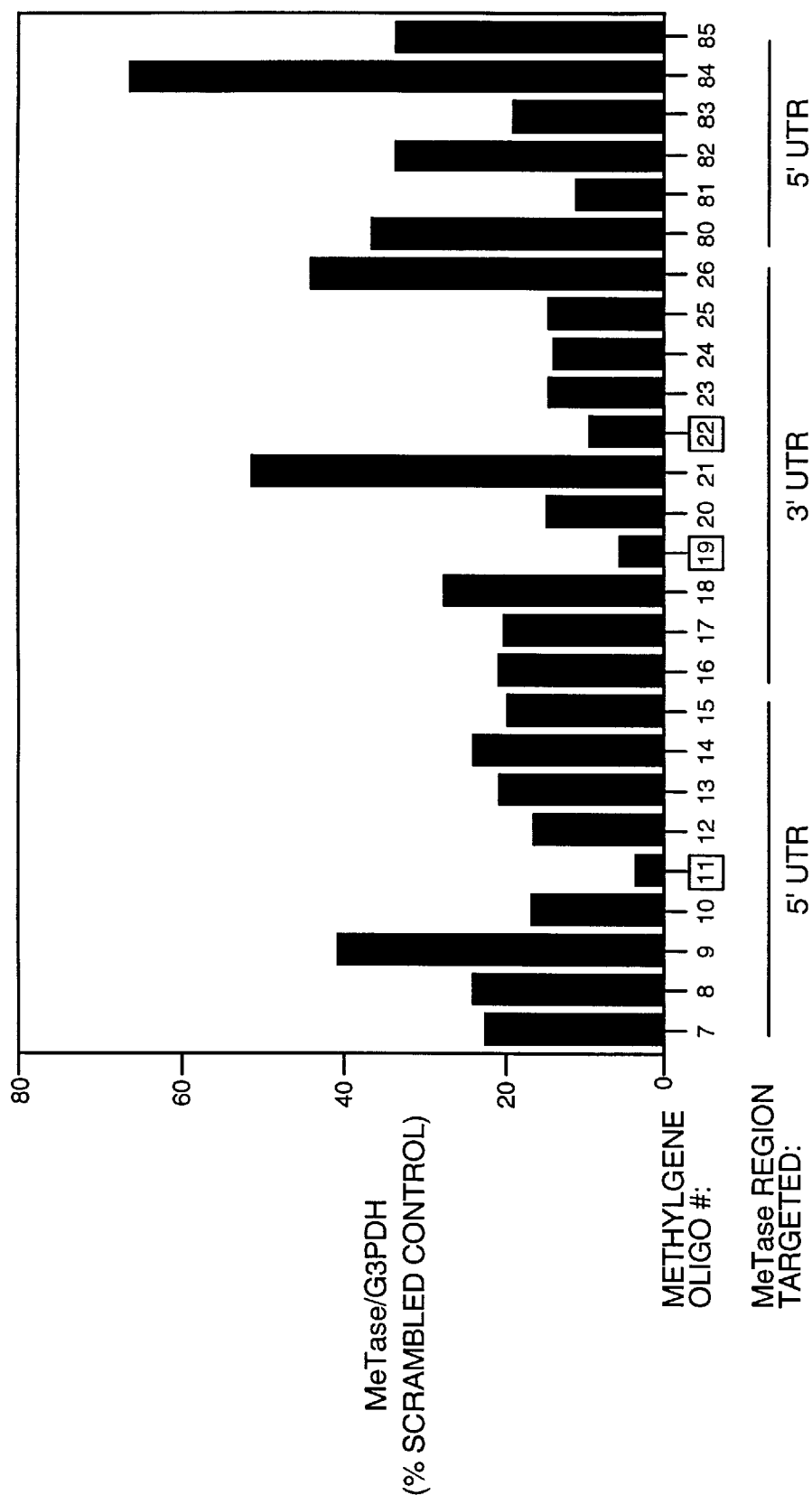
FIG. 3 is a graphic representation showing the ability of representative, nonlimiting, synthetic oligonucleotides of the invention to inhibit DNA MeTase activity in the nuclear extracts.

Cells were then harvested and washed twice with PBS and the nuclei were pelleted by centrifugation in an Eppendorf microfuge at 2,000 RPM for 15 min at 4° C. The nuclei were washed once in Buffer A and re-pelleted, then resuspended in 0.5 ml Buffer B (20 mM Tris pH 8.0, 0.25% glycerol, 1.5 mM MgCl$_2$, 0.5 mM PMSF, 0.2 mM EDTA 0.5 mM DTT and 0.4 mM NaCl). The resuspended nuclei were incubated on ice for 15 minutes then spun at 15,000 RPM to pellet nuclear debris. The nuclear extract in the supernatant was separated from the pellet and used for assays for DNA MeTase activity. For each assay, carried out in triplicate, 3 μg of nuclear extract was used in a reaction mixture containing 0.1 μg of a synthetic 33-base pair hemimethylated DNA molecule substrate with 0.5 μCi S-[methyl-$^3$H] adenosyl-L-methionine (78.9 Ci/mmol) as the methyl donor in a buffer containing 20 mM Tris-HCl (pH 7.4), 10 mM EDTA, 25% glycerol, 0.2 mM PMSF, and 20 mM 2-mercaptoethanol. The reaction mixture was incubated for 1 hour at 37° C. to measure the initial rate of the DNA MeTase. The reaction was stopped by adding 10% TCA to precipitate the DNA, then the samples were incubated at 4° C. for 1 hour and the TCA precipitates were washed through GFC filters (Fischer). Control were DNA samples incubated in the reaction mixture in the absence of nuclear extract, and nuclear extract incubated in the reaction mixture in the absence of DNA. The filters were laid in scintillation vials containing 5 ml of scintillation cocktail and tritiated methyl groups incorporated into the DNA are counted in a β-scintillation counter according to standard methods. To normalize and thus compare specific activity of the nuclear extracts from cells treated with various synthetic oligonucleotide both DNA MeTase and G3PDH activity were measured. FIG. 3 shows DNA MeTase enzymatic activity observed in A549 cells treated with synthetic oligonucleotides as indicated. Similar results were observed when using T24 cells. Note that values were expressed as a percentage of activity observed in cells treated with scrambled synthetic oligonucleotides. The results show that the treatment of cells with antisense oligonucleotides of the invention results in reduction in DNA MeTase activity in the nuclear extracts.

EXAMPLE 7

Inhibition of Tumor Growth in Vivo

Ten to twelve week old female BALB/c nude mice (Taconic Labs, Great Barrington, N.Y.) were injected subcutaneously in the flank area with 2×10$^6$ preconditioned A549 human lung carcinoma cells. Preconditioning of these cells was done by a minimum of three consecutive tumor transplantations in the same strain of nude mice. Subsequently, tumor fragments of approximately 25 mgs were excised and implanted subcutaneously in mice, in the left flank area under Forene anestesia (Abbott Labs., Geneva, Switzerland). When the tumors reached a mean volume of 100 mm$^3$, the mice were treated intravenously, by daily bolus infusion into the tail vein, with oligonucleotide saline preparations containing 2 mg/Kg of oligonucleotide according to the present invention. The optimal final concentration of the oligonucleotide is established by dose response experiments according to standard protocols.

Tumor volume was calculated according to standard methods every second day post infusion. (e.g., Meyer et al. Int. J. Cancer 43:851–856 (1989)). Treatment with the oligonucleotides of the invention caused a significant reduction in tumor weight and volume relative to controls treated with randomized or reverse antisense sequence (data not shown).

In addition, the activity of DNA MeTase enzyme was measured and found to be significantly reduced relative to randomer treated controls. These results show that the oligonucleotides according to the invention are capable of inhibiting MeTase enzymatic activity and tumor growth.

What is claimed is:

1. An oligonucleotide which inhibits DNA methyltransferase expression, the oligonucleotide having from 8 to 100 nucleotides and being complementary to a region of an RNA that encodes DNA methyltransferase, wherein the region includes 2 to 50 nucleotides selected from the nucleotide sequences set forth in the Sequence Listing as SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, AND SEQ ID NO 32.

2. The oligonucleotide according to claim 1, wherein the oligonucleotide has at least one internucleotide linkage selected from the group consisting of phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleotide linkages.

3. The oligonucleotide according to claim 2, wherein the oligonucleotide is a chimeric oligonucleotide comprising a phosphorothioate, phosphodiester or phosphorodithioate region and an alkylphosphonate or alkylphosphonothioate region.

4. The oligonucleotide according to claim 3, wherein the oligonucleotide comprises a ribonucleotide or 2'-O-substituted ribonucleotide region and a deoxyribonucleotide region.

5. A method for inhibiting tumor growth in a mammal comprising administering to the mammal, which has at least one tumor cell present in its body, an antisense oligonucleotide according to claim 1 under conditions where tumor growth is inhibited.

6. A method for inhibiting tumor growth in a mammal comprising administering to the mammal, which has at least one tumor cell present in its body, more than one antisense oligonucleotide according to claim 1 under conditions where tumor growth is inhibited.

7. An oligonucleotide having from 21 to 35 nucleotides, which inhibits DNA methyltransferase expression, and comprises a nucleotide sequence set forth in the Sequence Listings as SEQ ID NO 33, SEQ ID NO 34, SEQ ID NO 35, SEQ ID NO 36, SEQ ID NO 37, SEQ ID NO 38, SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50, SEQ ID NO 51, SEQ ID NO 52, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, or SEQ ID NO 64.

8. An oligonucleotide which inhibits DNA methyltransferase expression, the oligonucleotide having from 13 to 19 nucleotides from a nucleotide sequence set forth in the Sequence Listings as SEQ ID NO 33, SEQ ID NO 34, SEQ ID NO 35, SEQ ID NO 36, SEQ ID NO 37, SEQ ID NO 38, SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50, SEQ ID NO 51, SEQ ID NO 52, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, or SEQ ID NO 64.

* * * * *

UNITED STATES PATENT AND TRADEMARK OFFICE
CERTIFICATE OF CORRECTION

PATENT NO. : 6,020,318
DATED : February 1, 2000
INVENTOR(S) : Moshe Szyf et al.

It is certified that error appears in the above-identified patent and that said Letters Patent is hereby corrected as shown below:

<u>Title page, Item [73]</u>
Change the name of the Assignee from MethyGene, Inc., Canada to McGill University, Canada.

Signed and Sealed this

Twenty-first Day of August, 2001

Attest:

*Nicholas P. Godici*

NICHOLAS P. GODICI
*Acting Director of the United States Patent and Trademark Office*

*Attesting Officer*

```
                            SEQUENCE LISTING (1) GENERAL INFORMATION:

(iii) NUMBER OF SEQUENCES: 64

(2) INFORMATION FOR SEQ ID NO:1:

(i) SEQUENCE CHARACTERISTICS:
        (A) LENGTH: 4084 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:1:

TCTAGAGCTC GCGGCCGCGA CGTCAATTAA CCCTCACTAA AGGGAGTCGA CTCGATCGCC      60

CTATGTTGTC CAGGGCTGGA CTCGAACTCC TGCCCACAAG CCATCCTCCC ACCACAGCCT     120

CCTGAGTAGC TGGGGTTACA GGCACGCAGC ACCGCGGCAC TGCACCGGCT TTTGTTCTTT     180

TATTTTTTTC CCTCTTTGTC CCTGAAAGAG TCAAGCTACT AATTGTCAGT AATCAAATCA     240

GACCACGATT TCCCAGGCAA ACTCCTGGCA GTTCTACATT TAGGAATGAC TAGCTAGAGA     300

CATCCTGAAG AATGAGTTAT TCGGGGAGGC GCCACGACCT CCTCTAACTT CACCTCTATC     360

TGCCCTCTGT GTGGGTACCC CTTGCTTCCC TGGATGCTTG ACTCCCCCAT TTCATCCTCA     420

AAATGCCACC ACCCCCACC AGGCCTTTAG GAACATCAGC TGGCTGTTCC CCACAGTGTC      480

CTGTGGCCCT GGGCTACTCA TTCTGACACT GGCCATACTG TGGCACACCT TGTTATGGGC     540

TGTTGTCAGA CCCAACTGGA GAAAGACCAG CTGTAGGTCA TTTCCCTTAC GGGAGTGCCC     600

CAACTATATG ACCTGCCCCC TCTTTCCTGG TATCTTTTTG AGTCAGGGTC TCACTCTGTC     660

TCCTAGATTG GAGTGCAGTG ATGCAATCAC GGCTCACTGT GGCCTCGACC TCCCAGGCTC     720

AGGTGATCTT CTTCTCAGCC TCCCAAGTAA CTGGGACCAC AAGCACATGC CACCAAACCC     780

AGTTATTTTT ATTTTATTTT ATTTTATTTT ATTTTGAGAC AGAGTTTCAC TCTTGTTGCC     840

CAGGCTAGAG TGCAATGGTG TGACCAGCTC ACTGCAACCT CTGCCTCCCG GGTTCAAGTG     900

ATTCTCCTGC TCAGCCTCCA AGTTGCTGGG ATTACAGCCA CCCACCACCC ACGCCTGGCT     960

AATTTTTGTA TTTTTAGTAG AGATGGGGTT TCGCCATGTT GGCCAGGCTG GTCTCAAACC    1020

CTTGACCTCA GGTAATCCAC CCACCTTGGC CCTCAGGTAA TCCACCCAAC TGCTGCTGTA    1080

TGTTGGGATT CCAGGCATCA GCCACCACGC CCAGCCACTA ATTTTTGTAT TTTTGTAGAG    1140

ATGGAGTTTC GCCATGTTTC CCAGGCTGGT CTGAACGCCT GGGCTCAAGT GATCCGCTCG    1200

CCTTGGCCTC CCAAAGAGCT GGGATTATAA GCGTGAGCCA CCATGCCTGG TCTCTGGTAC    1260

CTTTTAAAAT ATACAGGCTG GGCATGATGG CTCATGCCTG TAATCCCAGC ACTTTGGGAG    1320

GCTGAGGCAG GTGGATCGCC TGAGGTCGGG AGTTCGAAAC CTAGCCTGAC CAACACGGAG    1380

AAACCCTGTC TCTGCTAAAA ATATAAAATT AGCTGGGTGA TGGTGGTGCA TGCCTGTAAT    1440
```

```
CCAGCTACTC GGGAGGCTGA GCCAGGAGAA TCGCTTGAAC CTGGGAGTCG GAGGTTTGAG      1500

CTGAGATCAC ACCATTGCAC TCCAGCCTGG GCAACAAGAG CAAAACCCTA TCTCAAAAAA      1560

AAAAAATATA TATATATATA TATATATATA TACACAGCTA TATATAGCGT ATATATATAT      1620

ACACACACAT ATGTATACAT ATATACGTAT GTATACACAT ATATACGTAT ATATACACAT      1680

ATATATGTAT ATATACACAC ATATACGTGT ATATATATAC GTGTATATAT ATATGCATGC      1740

CAGACAAGGT GACTCATGCC TGTAATCCTA GCACTTCAGG AGACTGAGGC AGGCGGATTC      1800

ACTTGAGGTC AGGAATCTAA GACCAGGCTT AACCAACATG GTGAAACCCT GTCTCTACTC      1860

AAAATACAAA AAATTAACGA GGCTGGTGGC ACCTATAATC CCAGCTACTT GGGAGGGCTG      1920

AGGTGAGAGA ATCACTTGAA CCCAGAAGGT GAGGGTTGCA GTGAGCTGAG ATCGCACCAC      1980

TGCACTCCAC CTGGGCAACA GAGCGAGACT CCATGTCTGT CTGTCTGTCT ATCTATCTGT      2040

ATAATGTATA TGTATGTATG TATATATGTG TGTGTATATA TATACACATA TATACATACA      2100

TATATACACA CATACTCTGT TACAGAGCTG CTGTGTGTGT GTGTATATAT ATATACACAT      2160

ATGTATATAT ACACATATAC ACATATATAT GTATATATAT ACACACATAT ATATACACAT      2220

ATATATGTAT ATATATACAC ACATATATAT ACACATATAT ATGATATATA TACACATATA      2280

TATGTATATA TATACACACA CACACACATA CACATAATTG TGTTACAGAG CTGCTATGTA      2340

ATCTCACAAT CATCAGAAAA ATGACCCCCA AAAGGGGAAC CTTGTTCAGA TCAGATGACT      2400

TCTTAGCATT AGGCATTCCA GTAGGACACT CTAGACTCTT GCGGGGAGAC AAAAGCCAGC      2460

TTAGTTTTTT CTAACACTCA TATGTTAAAC TTGTTTGTGT CCAAAACTTC TTTAGAACTG      2520

TGATATTCTT ACAGGCAAAT GAAGTTGCTT AACAAGTGTT TGTATTTTCT CCCCTATTTC      2580

TTCCTCCCAG GCTCAAAGAT TTGGAAAGAG ACAGCTTAAC AGAAAGGTA ATCTCCTCCT       2640

TAAAATTTTT CTTATTACCA AATCTGACTG ACACACTTTG TGGCTCATAA AAAGAAATTT      2700

GTTTTCTTTA AATGGATTTT GCATTTTTTC CCATGGAGTT TCAAAGATAA TTTGGATATT      2760

CTTGTTAAAT GTCAGCACTA ATTTGCTGCT AATAGTTGGG TGGTGGTGGT GTTTTTTTTT      2820

GTTGTTGTTT TTGTTTTTTG AGACAGAGTC TCACTCTGTC ACCCAGGCTA GAGTGCAATG      2880

GCATGATCTC GGCCTCACTG TGACCTCTGC CTCCCGGATT CAAGCTGTTC TCCTGCCTCA      2940

GCCTCCCAAG TAGCTCTAAC TACAGGCTCA AGCCACCATG CCCAGCTAAT TTTTAAATAT      3000

TTTTTGTAAA GATGGGATTT TGTCATGTTG CCCCAGGCTG GTCTTGAACT CTGGGGCTCA      3060

AAGCAATCCA CTTGCCTCGG CCTCCCAAAG TGCTGGGATT ATAGGTGTGA GCCACTGTGC      3120

CTGGCCCAGA CATTTACAGA AGCACAGTAT TATTCTTATA AACCATGATA TGTCTCCATC      3180

TCACCTCCAG CTTTCCCATT TTTCACCACT TTGGAGACAG GAGTGAAGTG ATCCTAATGG      3240

AAATTCCCTG AACACATTTC ATGACTGTTT AGTGTTTTGA CTGAGACAGC ATTGCCTGCC      3300

ATTCACTCAT TGTGATGTGA TCAGGCAGCT CAATAATTTG TGTATTAGTC CACTAGTGAA      3360

TAGCTTGGGA ATGTGGGTAC TGCTAAACCT ATATCCTTCC CTTAGGAATG TGTGAAGGAG      3420

AAATTGAATC TCTTGCACGA ATTTCTGCAA ACAGAAATAA AGAATCAGTT ATGTGACTTG      3480

GAAACCAAAT TACGTAAAGA AGAATTATCC GAGGTAAGTC AGTTCTCAGC ATCCTAGCCT      3540

CTAGAAAAAT GTCTCCTCCT AGTAACTTGT CTGTGACCAG GGAGGCAGCA AGATCCCCAG      3600

CTGTCCTCAT TGCCTGATGA TGATGATGAT GATGATGATG ATGAAGAACA CATGTGTTCT      3660

GTCTCTGACA CGTGTTACAT TCACTGCTAC TAATTATCCT GTCCTGCTGT AGGAGGGCTA      3720

CCTGGCTAAA GTCAAATCCC TGTTAAATAA AGATTTGTC CTTGAGAACG GTGCTCATGC       3780

TTACAACCGG AAGTGAATGG ACGTCTAGAA AACGGGAACC AAGCAAGAAG TGAAGCCCGT      3840
```

```
AGAGTGGGAA TGGCAGATGC AACAGCCCC CCCAAACCCC TTTCCAAACC TCGCACGCCC       3900

AGGAGGAGCA AGTCCGATGG AGAGGCTAAG CGTAAGAGCA GATGATTCCT TTTATTTTTA      3960

ATTGTTTTTG AGATGGAGTC TCACTGTGTT GCCCAGTCTG GAGCACAGTG GTGTAACCTC      4020

GGCTCACTGT AACCTCTGCC TCCAGGTTCA AGAGACCCTC CTGCCTCAGC CTCCCAAGTA      4080

ACTG                                                                   4084

(2) INFORMATION FOR SEQ ID NO:2:

(i) SEQUENCE CHARACTERISTICS:
        (A) LENGTH: 348 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:2:

GCCAACATTA GCAAGCTGGT TGTTGACTAG AATAAAAATG CAAAGATGCT AGTCCTTAGA       60

ACCTGGGCTT CCTGCAATAG CTTAGTAATG TTGAACTGCA TTATTGCTGT GGGCTTTCTA      120

TTGATAGTGG CTTTTTTTTT TCTTTTTAAT GCTTTTTCTT CTTTAAACAG CTGAACCTTC      180

ACCTAGCCCC AGGATTACAA GGAAAAGCAC CAGGCAAACC ACCATCACAT CTCATTTTGC      240

AAAGGGGTCA GTATACGATA AATTGGCGGC TGCCTTTTTT AGGGGCCGGC TGTTTTGGGA      300

TGGAATTGGT AGGGCGTCAC GTGGCAATTC TGTCTTCCGT GTTGTATA                   348

(2) INFORMATION FOR SEQ ID NO:3:

(i) SEQUENCE CHARACTERISTICS:
        (A) LENGTH: 454 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:3:

TCTCTGACAC TAGCAGCTGT TGATCGGTGT TTAGACCCGT GATTTCTTAG GACTTACAAG       60

ATGGCAAGAC AACATTCTAA ACCCGTCATT CAGAGAAACA TTAAACTTGA AGCCTCTTTC      120

AACATCCTGG TGAATGAGGG TCCACTTCAG GCCAGCTGGA GGCCTAGGGT CTTGTTCCAC      180

TAATGGTTGG CCTCACTGTG TGTGACAGCC CTGCCAAACG GAAACCTCAG GAAGAGTCTG      240

AAAGAGCCAA ATCGGATGAG TCCATCAAGG AAGAAGACAA AGACCAGGTA GGGCCAGTGC      300

TTTCATTTCC TGACTCTACC TTACTTGGTG TATTTGATGA TTGTGACTTC ATATGTGTTC      360

TGTCCAAGTA AATAAAAACC CTGTCTAGGG CTCTATTTAG GGCTCTCCAG AGAGACAGGA      420

CCAATAGAAT GTATATGTGT GTATCAACGT ATAG                                  454

(2) INFORMATION FOR SEQ ID NO:4:

(i) SEQUENCE CHARACTERISTICS:
        (A) LENGTH: 227 base pairs
        (B) TYPE: nucleic acid
        (C) STRANDEDNESS: both
        (D) TOPOLOGY: linear
```

(ii) MOLECULE TYPE: other nucleic acid (iii) HYPOTHETICAL: NO (iv) ANTI-SENSE: NO (xi) SEQUENCE DESCRIPTION: SEQ ID NO:4:

GTTTTGGGGT TGGTGGGGAT TAATACCAGA GTAAGAGTTT CTCAGATCTT CTCCCCTTTT     60

CCCAGGCCCC TTCTTTTCCC ACTCTTGCTC TAACCATGTC AAATGTGTTA ATATTTCAAC    120

TCACACTTTT GGTGTTGACC TTCCCTTGAA ACCAGTATTC TAATCTTTTT TGTTCTTCCT    180

TCCCTCCACA CAGGATGAGA AGAGACGTAG AGTTACATCC AGAGAAC                  227

(2) INFORMATION FOR SEQ ID NO:5:

(i) SEQUENCE CHARACTERISTICS:
             (A) LENGTH: 223 base pairs
             (B) TYPE: nucleic acid
             (C) STRANDEDNESS: both
             (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:5:

CAGGGCTCCG AGATAAGTAA GATTGCTTTT GGGGAAAAGA GGAGCTTTAT GAAAACTGCT     60

TCTTTGGGGA AGCTCCTGGC ACTCACACTT GGGGTCTGTG TTATTTTGCT TGACAGAGTT    120

GCTAGACCGC TTCCTGCAGA AGAACCTGAA AGAGCAAAAT CAGGAACGCG CACTGAAAAG    180

GAAGAAGAAA GAGATGAAAA AGTAAAGCTC TATCACCTCT AAG                      223

(2) INFORMATION FOR SEQ ID NO:6:

(i) SEQUENCE CHARACTERISTICS:
             (A) LENGTH: 34 base pairs
             (B) TYPE: nucleic acid
             (C) STRANDEDNESS: both
             (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:6:

AAGAAAAGAG ACTCCGAAGT CAAACCAAAG AACC                                 34

(2) INFORMATION FOR SEQ ID NO:7:

(i) SEQUENCE CHARACTERISTICS:
             (A) LENGTH: 289 base pairs
             (B) TYPE: nucleic acid
             (C) STRANDEDNESS: both
             (D) TOPOLOGY: both (ii) MOLECULE TYPE: DNA (genomic)

(v) FRAGMENT TYPE: linear (xi) SEQUENCE DESCRIPTION: SEQ ID NO:7:

TGAGTCCTGA GTAGTAAATC GTCTGGCTTC CTGCAGTGAA GACAGGAGAG GCAGCCTGTC     60

CTCTGAACCT GGGGAGGAGC TTGTGTCAGC CCTTAGGAGC TGTTGGCCCC GGTGCAGGGC    120

```
CCCCCCCGAG CTGACCAGCC TGTGTGTGTG TTGTCTTCTG TGACAGAACA CCCAAACAGA      180

AACTGAAGGA GGAGCCGGAC AGAGAAGCCA GGGCAGGCGT GCAGGCTGAC GAGGACGAAG      240

ATGGAGACGA GAAAGATGAG AAGAAGCACA GAAGTCAACC CAAAGATCT                  289
```

(2) INFORMATION FOR SEQ ID NO:8:

(i) SEQUENCE CHARACTERISTICS:
        (A) LENGTH: 132 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:8:

```
GTGGTTAGTG TTTCTAAGCT GCTACTTGCT GTGTATCTGT TCACCCTGCA GAGCTGCCAA      60

ACGGAGGCCC GAAGAAAAAG AACCTGAAAA AGTAAATCCA CAGATTTCTG ATGAAAAGA       120

CGAGGATGAA AA                                                          132
```

(2) INFORMATION FOR SEQ ID NO:9:

(i) SEQUENCE CHARACTERISTICS:
        (A) LENGTH: 80 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:9:

```
GGAGGAGAAG AGACGCAAAA CGACCCCCAA AGAACCAACG GAGAAAAAAA TGGCTCGCGC      60

CAAAACAGTC ATGAACTCCA                                                  80
```

(2) INFORMATION FOR SEQ ID NO:10:

(i) SEQUENCE CHARACTERISTICS:
        (A) LENGTH: 141 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:10:

```
GCTCACGAGG CGGCTGGGAG CTGCTCTCTG AGTGCCATCA TCTGTGTTCC TGCTCCCACA      60

GACCCACCCT CCCAAGTGCA TTCAGTGCGG GCAGTACCTG GACGACCCTG ACCTCAAATA      120

TGGGCAGCAC CCACCAGACG C                                                141
```

(2) INFORMATION FOR SEQ ID NO:11:

(i) SEQUENCE CHARACTERISTICS:
        (A) LENGTH: 167 base pairs
        (B) TYPE: nucleic acid
        (C) STRANDEDNESS: both (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:11:

GGTGGATGAG CCACAGATGC TGACAAATGA GAAGCTGTCC ATCTTTGATG CCAACGAGTC         60

TGGCTTTGAG AGTTATGAGG CGCTTCCCCA GCACAAACTG ACCTGCTTCA GGTAAGTGCA        120

CTTTCGTGTG CATGTTTGCT TCGTGGAAGG AGGCACATCC CCAGAGG                     167

(2) INFORMATION FOR SEQ ID NO:12:

(i) SEQUENCE CHARACTERISTICS:
        (A) LENGTH: 321 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:12:

CCTCGTGCCT GATATGAAGT CTGCACGAAG ACGCCCTTCA CGGCTTAGCT GGTAAGCATG         60

TGCTTTGTTT CCTGTCTAGT GTGTACTGTA AGCACGGTCA CCTGTGTCCC ATCGACACCG        120

GCCTCATCGA GAAGAATATC GAACTCTTCT TTTCTGGTTC AGCAAAACCA ATCTATGATG        180

ATGACCCGTC TCTTGAAGGT AAGGAATAGT CCGGGATTAT GTTTGGGGCA CACTTTAAAA        240

ACAGCCAGGC AGGTTGGCTC ACATCTGTAA TCCTAGCACT TTGGGGGCTG AGGCCAGAGG        300

ATCACTTGAG CCCGGGAGTT T                                                 321

(2) INFORMATION FOR SEQ ID NO:13:

(i) SEQUENCE CHARACTERISTICS:
        (A) LENGTH: 293 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:13:

TTTAGTCCAT TTCCTTTTTC TGCTCTAGGT GGTGTTAATG GCAAAAATCT TGGCCCCATA         60

AATGAATGGT GGATCACTGG CTTTGATGGA GGTGAAAAGG CCCTCATCGG CTTCAGCACC        120

TGTAAGTGTG TGGCCCATCA TAGGCTGGCC GGGGTCTGAA AGGGGCCTTC ATGTTCTCCT        180

TCCTGGGGGC TGACGGGGCT CTGGTGGGAA TTCTCAGCAG GCTTGCAGAA GGCCATGTGA        240

CTGGGAACCT TAGCAGGTTC AGTTGGGGTA GATCTCTTGT GTTAGTTAGT AGG              293

(2) INFORMATION FOR SEQ ID NO:14:

(i) SEQUENCE CHARACTERISTICS:
        (A) LENGTH: 1094 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:14:

| | | | | | |
|---|---|---|---|---|---|
| CGCTCTCTGG | CTGGCTCAGA | CAGGCTTCTT | CAGAACAAGC | CAGCTATGAT | GTGTTGTGCC | 60 |
| CTATGTTTCT | GACATTTGGG | TACGGGATGA | CTTTTAGACT | GTTGGGTGAG | TTTGGTAGAC | 120 |
| TCCTCCATGC | CCTGTGGCCA | CTGTAGGCGC | CATCAGATTC | CAGCCCCTTT | TCCACACCTC | 180 |
| CTCTGTTCGC | CCCAGCATTT | GCCGAATACA | TTCTGATGGA | TCCCAGTCCC | GAGTATGCGC | 240 |
| CCATATTTGG | GCTGATGCAG | GAGAAGATCT | ACATCAGCAA | GATTGTGGTG | GAGTTCCTGC | 300 |
| AGAGCAATTC | CGACTCGACC | TATGAGGACC | TGATCAACAA | GATCGAGGTA | AGAGATCGAG | 360 |
| GGTCCTCAGC | ATCCGGGATT | CCCACTGGAA | ACTTGCCTTC | AGAACCAGCA | GACACTGTTC | 420 |
| TTCAGTTGGA | TTTAGGCCAG | TTTGGCTTAA | GCATGAGAGA | AACCTGTTCT | CTTTCAAGAC | 480 |
| CACGGTTCCT | CCTTCTGGCC | TCAACTTGAA | CCGCTTCACA | GAGGACTCCC | TCCTGCGACA | 540 |
| CGCGCAGTTT | GTGGTGGAGC | AGGTGGAGAG | TTATGACGAG | GCCGGGACA | GTGATGAGCA | 600 |
| GCCCATCTTC | CTGACGCCCT | GCATGCGGGA | CCTGATCAAG | CTGGCTGGGG | TCACGCTGGG | 660 |
| ACAGAGGTAA | GGATGCGGCT | GGGACCAGAG | TGAAGACTGG | AGACCGGGGA | GGGTAGAGCA | 720 |
| TGGCCCACAT | CCTCTGTCCC | AGTCCTCTGA | GATGCTGGAA | CCTCTCCCGT | AGGCGAGCCC | 780 |
| AGGCGAGGCG | GCAGACCATC | AGGCATTCTA | CCAGGGAGAA | GGACAGGGGA | CCCACGAAAG | 840 |
| CCACCACCAC | CAAGCTGGTC | TACCAGATCT | TCGATACTTT | CTTCGCAGAG | CAAATTGAAA | 900 |
| AGGATGACAG | AGAAGACAAG | GAGAACGCCT | TTAAGCGCCG | GCGATGTGGC | GTCTGTGAGG | 960 |
| TAACCTCACC | TGTGGGTGCT | CCCGCTCCCC | TAAGGTGGCC | CAGCCTCTGG | CCTGATCTGA | 1020 |
| GGACTGCTCC | ATCTTTCTCT | GTGGCTTGAG | ACTCTGGCTG | CTCAAATGTG | ACCCTGAGAC | 1080 |
| AGAAATTGTT | GTGG | | | | | 1094 |

(2) INFORMATION FOR SEQ ID NO:15:

(i) SEQUENCE CHARACTERISTICS:
      (A) LENGTH: 206 base pairs
      (B) TYPE: nucleic acid
      (C) STRANDEDNESS: both
      (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:15:

| | | | | | |
|---|---|---|---|---|---|
| AGGTGTGTCA | GCAGCCTGAG | TGTGGGAAAT | GTAAAGCCTG | CAAGGACATG | GTTAAATTTG | 60 |
| GTGGCAGTGG | ACGGAGCAAG | CAGGCTTGCC | AAGAGCGGAG | GTAGGTCAGG | CCGAGTCTTC | 120 |
| CTCCTGTGGC | AGAGGACTTG | CCAGCTGGTG | GCAGATGCAC | TGTGGAGAAG | GGCCGTCATG | 180 |
| TGTGGGACAG | CACCAGGATT | CCTTCG | | | | 206 |

(2) INFORMATION FOR SEQ ID NO:16:

(i) SEQUENCE CHARACTERISTICS:
      (A) LENGTH: 268 base pairs
      (B) TYPE: nucleic acid
      (C) STRANDEDNESS: both
      (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:16:

| | | | | | |
|---|---|---|---|---|---|
| AGACCTGTCC | CTGTTATGAA | GAAAACAGCC | CCGGTTGGTC | TTACTTAGAA | AAGGGGCCTT | 60 |
| AGGTATAACC | AGTGACATTG | CAGGTGTCCC | AATATGGCCA | TGAAGGAGGC | AGATGACGAT | 120 |
| GAGGAAGTCG | ATGATAACAT | CCCAGAGATG | CCGTCACCCA | AAAAAATGCA | CCAGGGGAAG | 180 |
| AAGAAGAAAC | AGAACAAGAA | TCGCATCTCT | TGGGTCGGAG | AAGCCGTCAA | GGTAACCCTT | 240 |
| GGAGTCCCCT | TGGTTCAGTC | CTCACTGC | | | | 268 |

(2) INFORMATION FOR SEQ ID NO:17:

(i) SEQUENCE CHARACTERISTICS:
        (A) LENGTH: 241 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:17:

| | | | | | |
|---|---|---|---|---|---|
| AAGTCAAGGC | CAGCAAAGAC | CCTCAGAATG | ATCCTCCATG | AACTTATGCT | CTCATTTTCA | 60 |
| GACTGATGGG | AAGAAGAGTT | ACTATAAGAA | GGTGTGCATT | GATGCGGAAA | CCCTGGAAGT | 120 |
| GGGGGACTGT | GTCTCTGTTA | TTCCAGATGA | TTCCTCAAAA | CCGCTGTATC | TAGCAAGGTT | 180 |
| TGCATCTTTC | TTTTTGCTTG | ACTTCTGCAT | GCACTTTCTC | ATCAAGTAGG | AGATGCCCTG | 240 |
| T | | | | | | 241 |

(2) INFORMATION FOR SEQ ID NO:18:

(i) SEQUENCE CHARACTERISTICS:
        (A) LENGTH: 258 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:18:

| | | | | | |
|---|---|---|---|---|---|
| CTCCCCATGC | CCGTCTTCTA | TTCCAGGGTC | ACGGCGCTGT | GGGAGGACAG | CAGCAACGGG | 60 |
| CAGATGTTTC | ACGCCCACTG | GTTCTGCGCT | GGGACAGACA | CAGTCCTCGG | GGCCACGTCG | 120 |
| GACCCTCTGG | AGCTGTTCTT | GGTGGATGAA | TGTGAGGACA | TGCAGCTTTC | ATATATCCAC | 180 |
| AGCAAAGTGA | AAGTCATCTA | CAAAGCCCCC | TCCGAAAACT | GGGCCATGGA | GGTGAGTGCC | 240 |
| TGGTGTCCTC | GTGAGCCC | | | | | 258 |

(2) INFORMATION FOR SEQ ID NO:19:

(i) SEQUENCE CHARACTERISTICS:
        (A) LENGTH: 241 base pairs
        (B) TYPE: nucleic acid
        (C) STRANDEDNESS: both (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:19:

```
GACCCAACCG ACGATATCTT TGAGTCTCCC AAGGGAGGCA TGGATCCCGA GTCCCTGCTG     60

GAGGGGGACG ACGGGAAGAC CTACTTCTAC CAGCTGTGGT ATGATCAAGA CTACGCGAGA    120

TTCGAGTCCC CTCCAAAAAC CCAGCCAACA GAGGACAACA AGTTCAAGTG AGCACTGGGG    180

CTGGACTCGG GGTCAGCAGG CACTTTCAGC CCACATCACT CCCTTTTCCC GTGTGCTTCC    240

G                                                                   241
```

(2) INFORMATION FOR SEQ ID NO:20:

(i) SEQUENCE CHARACTERISTICS:
         (A) LENGTH: 282 base pairs
         (B) TYPE: nucleic acid
         (C) STRANDEDNESS: both
         (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:20:

```
AAGCTGGCAG TAGCTGCTGC GGCCACTGCC GGCCACCTCA GGGCCTTATG TTTCTGTCCC     60

TTTGTTTCCT TCAGATTCTG TGTGAGCTGT GCCCGTCTGG CTGAGATGAG GCAAAAAGAA    120

ATCCCCAGGG TCCTGGAGCA GCTCGAGGAC CTGGATAGCC GGGTCCTCTA CTACTCAGCC    180

ACCAAGAACG GCATCCTGTA CCGAGTTGGT GATGGTGTGT ACCTGCCCCC TGAGGCCTTC    240

ACGTTCAAGT AAGTGCCCCC TCGGAGCAGC CGGGGCCAGG GG                       282
```

(2) INFORMATION FOR SEQ ID NO:21:

(i) SEQUENCE CHARACTERISTICS:
         (A) LENGTH: 433 base pairs
         (B) TYPE: nucleic acid
         (C) STRANDEDNESS: both
         (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:21:

```
AAATCATTTC TTAGGGTACA CACCTACCTT AATTCATCAG GTGCTTGACT TTAAATGGTT     60

ATTTTCACTG GTCAGTCATG CCTGACTGAC CACTGCAAGG TGGAAGGTTC ATTGATGTCA    120

AGTGGGTGCT TCTCTGCAGC ATCAAGCTGT CCAGTCCCGT GAAACGCCCA CGGAAGGAGC    180

CCGTGGATGA GGACCTGTAC CCAGAGCACT ACCGGAAATA CTCCGACTAC ATCAAAGGCA    240

GCAACCTGGA TGCCCCTGAG CCCTACCGAA TTGGCCGGAT CAAAGAGATC TTCTGTCCCA    300

AGAAGAGCAA CGGCAGGCCC AATGAGACTG ACATCAAAAT CCGGGTCAAC AAGTTCTACA    360

GGTCAGCAGA GGCCTCTGTT CTTCCTCGAG GCCACAGACT CTTCTAGAAG GCTCTGCTGA    420

AACAAGGTTG TGG                                                      433
```

(2) INFORMATION FOR SEQ ID NO:22:

(i) SEQUENCE CHARACTERISTICS:
        (A) LENGTH: 394 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:22:

```
AAAAGGAGAG CTCCTAACGA GGCCTACTCC CGCTCGCAGG CCTGAGAACA CCCACAAGTC      60
CACTCCAGCG AGCTACCACG CAGACATCAA CCTGCTCTAC TGGAGCGACG AGGAGGCCGT     120
GGTGGACTTC AAGGCTGTGC AGGGCCGCTG CACCGTGGAG TATGGGGAGG ACCTGCCCGA     180
GTGCGTCCAG GTGTACTCCA TGGGCGGCCC CAACCGCTTC TACTTCCTCG AGGTGGTGCC     240
CCTGCTTGCT AGAGGGAAGG CTTCGGGGTC AAAGTTGGCC AGAAGGAGTC TGATGTCGGG     300
TTATACACAA GGCGGCTTGG CTGCAGGGTT TCAGCTTTTG TAAGAAGTGG GTGGTTGGCT     360
GACGTGAAGC TGTTCTGCAG GAGCTTTACG GGGG                                 394
```

(2) INFORMATION FOR SEQ ID NO:23:

(i) SEQUENCE CHARACTERISTICS:
        (A) LENGTH: 671 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:23:

```
GTCAACTACT CTATTGGTGG CTAATTGGTC ATGGCCCCAC TGAGGAGAAT TAAGTGACTA      60
TCAATTGCCT TCTTACTAGT CTGCGTTAGA GAGGGGACAG TGGCGTTTCT CTCCCAAACG     120
ATTGCAGTTC TCTCCTTTTC AGGCCTATAA TGCAAAGAGC AAAAGCTTTG AAGATCCTCC     180
CAACCATGCC CGTAGCCCTG GAAACAAAGG GAAGGGCAAG GGAAAAGGTA CGTCATTGTA     240
TGAGTTTCTT TTCAAGTTAT TCTTCTGTAA CTTGGAGGCT GCCTGTGAAT CCCTCAGTGT     300
AAAACCACCT CTGGTGTTAC TGACTCTGGG ACAGCGAGGC CGCCTGAGTT AACAAGGCGC     360
TTGAGAGCAA GGTGGACTTG GACTCTGAGG ATCGGGTTTA GCCTCTGGCC TCTCTCCCCC     420
AGGGAAGGGC AAGCCCAAGT CCCAAGCCTG TGAGCCGAGC GAGCCAGAGA TAGAGATCAA     480
GCTGCCCAAG CTGCGGACCC TGGATGTGTT TTCTGGCTGC GGGGGGTTGT CGGAGGGATT     540
CCACCAAGCA GGTGAGCGCC CGTAGGCTCC ATCTCTGAAT ACCTGGTGAG CCCAGACCGG     600
GCAGGTGCTA CCTGAAACGA CTTCCAACCC GGTCACCTTC TGATCTAAGA ATCTCTTCGA     660
GGCCAGGCAC G                                                          671
```

(2) INFORMATION FOR SEQ ID NO:24:

(i) SEQUENCE CHARACTERISTICS:
        (A) LENGTH: 451 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:24:

ACTGCACGCC AGCCTGGGTG ACAGAGCGAG ACTCCATCTC AAAAAAAAAA AAAAAATCTT      60

CTGGAGAGTT GAAAGCATGG CTTCGTGCTT GATCTGCCAG CATCTCTGAC ACGCTGTGGG     120

CCATCGAGAT GTGGGACCCT GCGGCCCAGG CGTTCCGGCT GAACAACCCC GGCTCCACAG     180

TGTTCACAGA GGACTGCAAC ATCCTGCTGA AGCTGGTCAT GGCTGGGGAG ACCACCAACT     240

CCCGCGGCCA GCGGCTGCCC CAGAAGGGAG ACGTGGAGAT GCTGTGCGGC GGGCCGCCCT     300

GCCAGGGCTT CAGCGGCATG AACCGCTTCA ATTCGCGCAC CTACTCCAAG TTCAAAAACT     360

CTCTGGTGGT TTCCTTCCTC AGGTAAACGG GTAGAAGCCC CCCAGTGTTG CCAGACGGCC     420

CGGGGCTGTG CGCATGTCAG CAGTGTCATT T                                    451

(2) INFORMATION FOR SEQ ID NO:25:

(i) SEQUENCE CHARACTERISTICS:
            (A) LENGTH: 434 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:25:

GAAGCTCACA GCTCAGCTCT CACCAGGGAG AGACTTTGAT AACATTCGTG AGGGGCTTCC      60

GGCACAGTGG GCGTTTCTTC CCTCTGTCTG TGGAGGTGAC TCCTGCAGTC TCTCCTGCCC     120

CCTACAGCAG CTACTGCGAC TACTACCGGC CCCGGTTCTT CCTCCTGGAG AATGTCAGGA     180

ACTTTGTCTC CTTCAAGCGC TCCATGGTCC TGAAGCTCAC CCTCCGCTGC CTGGTCCGCA     240

TGGGCTATCA GTGCACCTTC GGCGTGCTGC AGGTGGGCCC TGGGGCTGGG GCGGGCAGAC     300

AGATGAGGCC AGCACGTGAC CCGGCCAGCA GCCAGCCATC CCTTACTGAA GGCAGGGTTC     360

AATGGCATAG GCCTGCCATC CAGGCAGCAG AGGCTGGCAT GGTGCTCTGT CCACTGGCGG     420

ATGAGGGGAG ATCG                                                       434

(2) INFORMATION FOR SEQ ID NO:26:

(i) SEQUENCE CHARACTERISTICS:
            (A) LENGTH: 317 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:26:

CGACTCAGCT GCTGACCCTG GGCCTGGGTC TGGCCAGTCC AGTTGGGAGT GTCCCACTGA      60

CGGTGGGGTT GTCCGTCCTT CTCCCCCACA GGCCGGTCAG TACGGCGTGG CCCAGACTAG     120

GAGGCGGGCC ATCATCCTGG CCGCGGCCCC TGGAGAGAAG CTCCCTCTGT TCCCGGAGCC     180

```
ACTGCACGTG TTTGCTCCCC GGGCCTGCCA GCTGAGCGTG GTGGTGGATG ACAAGAAGTT      240

TGTGAGCAAC ATAACCAGGT AGGTGGCCCC CGTCGCTCCT CCACACACTG CCGACGAGGC      300

CTCAGTAGCT CATGGGG                                                     317
```

(2) INFORMATION FOR SEQ ID NO:27:

(i) SEQUENCE CHARACTERISTICS:
        (A) LENGTH: 489 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:27:

```
CATAGCCCCA TCCCCCCTTC CAGATGGCAT CCAGCACACT GCCACCCATG TGACCTCGGG       60

CAGTGCTGTG ATCTCGGGAG AAGGCCATCT GAGCAGGCAG GGGGTGGCAC CTGTGATGAG      120

GGGACAGCTG CTGCGTGCAT CTCCAGAGGT GTTGACCTCC TCCTCTGTTG CAGGTTGAGC      180

TCGGGTCCTT TCCGGACCAT CACGGTGCGA GACACGATGT CCGACCTGCC GGAGGTGCGG      240

AATGGAGCCT CGGCACTGGA GATCTCCTAC AACGGGGAGC CTCAGTCCTG GTTCCAGAGG      300

CAGCTCCGGG GCGCACAGTA CCAGCCCATC CTCAGGGACC ACATCTGTAA GGTAATGGCA      360

CCCTGACAGA GCGGCTCCTC CTCGAGGCCC AGCCCAGCAG CCTCGTGGGA ACAGTCAGCC      420

TGCCCAAGAC TCAGGGGAGA CATGGAATCT GATCCCAGGC TCCTCCTCCG AGTCTCAGCC      480

TTTGTGTGA                                                              489
```

(2) INFORMATION FOR SEQ ID NO:28:

(i) SEQUENCE CHARACTERISTICS:
        (A) LENGTH: 285 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:28:

```
ATGGACACGT CCCCCCACAC TCTTTCAGGA CATGAGTGCA TTGGTGGCTG CCCGCATGCG       60

GCACATCCCC TTGGCCCCAG GGTCAGACTG GCGCGATCTG CCCAACATCG AGGTGCGGCT      120

CTCAGACGGC ACCATGGCCA GGAAGCTGCG GTATACCCAC CATGACAGGA AGAACGGCCG      180

CAGCAGCTCT GGGGCCCTCC GTGGGGTCTG CTCCTGCGTG GAAGGTGGGT CCTGTAAGTT      240

GTGGTTCCCG GTGGCTGAGG GGAAGGAAGG CAGACCTGGG CCTTT                      285
```

(2) INFORMATION FOR SEQ ID NO:29:

(i) SEQUENCE CHARACTERISTICS:
        (A) LENGTH: 382 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:29:

GACAGAGTGC CATCTCTGCC TCCCAAAGCT CTAAGAGCCA TGTCCCAAGC CTATACCCCA      60

TCCCACAACT GCAGCCTCAT CACTGTCCTG TCTTCCAGCC GGCAAAGCCT GCGACCCCGC     120

AGCCAGGCAG TTCAACACCC TCATCCCCTG GTGCCTGCCC CACACCGGGA ACCGGCACAA     180

CCACTGGGCT GGCCTCTATG GAAGGCTCGA GTGGGACGGC TTCTTCAGCA CAACCGTCAC     240

CAACCCCGAG CCCATGGGCA AGCAGGTAGG TGGGGAGGGG GCATCCGAGG GCCTGGGTCA     300

GGCTGTACTT GGCGGCCTAA CTAGGTGGAA GTGTGGGTTT AGCCAAGTGG GGGACAGCAC     360

CCCAGGATCC CCCAGGCACC TG                                             382

(2) INFORMATION FOR SEQ ID NO:30:

(i) SEQUENCE CHARACTERISTICS:
                (A) LENGTH: 352 base pairs
                (B) TYPE: nucleic acid
                (C) STRANDEDNESS: both
                (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:30:

AGACTGCTCT GCCTCCTGCC CCTCCACGTC CACGGACAAG CTCATAGCCA AGCCATGGCC      60

GTATGCTGTC ACAGTGCCAT TTCCCTCCCT GTCCCCGACG GTGACCCGGC CTGGGTGCTA     120

CTGCCCTCGC CCACCGCGCC TCTTTCCCCC AGGGCCGCGT GCTCCACCCA GAGCAGCACC     180

GTGTGGTGAG CGTGCGGGAG TGTGCCCGCT CCCAGGGCTT CCCTGACACC TACCGGCTCT     240

TCGGCAACAT CCTGGACAAG CACCGGCAGT CAGTGGGGCG GCGCGCTGGG TCTGGACAGG     300

AAGGAGGCTT CTGTGCCTGT CACCAGGTGG GGCTGGGGCA GCGCAGTCAC TT             352

(2) INFORMATION FOR SEQ ID NO:31:

(i) SEQUENCE CHARACTERISTICS:
                (A) LENGTH: 254 base pairs
                (B) TYPE: nucleic acid
                (C) STRANDEDNESS: both
                (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:31:

CAATGCCCAG GTTGTCCTCC ATCTGAGCAG GTGCTGGAGT ACACCTCCCC CGGCCTTGGG      60

CCTGGTGTCC ACATCAGGCA TTGCCCTTCT CCCCTCCTGC AGGTGGGCAATGCCGTGCCA     120

CCGCCCCTGG CCAAAGCCAT TGGCTTGGAG ATCAAGCTTT GTATGTTGGC CAAAGCCCGA     180

GAGAGTGCCG TATGGTGGGG TGGGCCAGGC TTCCTCTGGG GCCTGACTGC CCTCTGGGGT     240

ACATGTGGGG GCAG                                                      254

(2) INFORMATION FOR SEQ ID NO:32:

(i) SEQUENCE CHARACTERISTICS:

(A) LENGTH: 565 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:32:

ACTGAGCCTC TGGGTCTAGA ACCTCTGGGG ACCGTTTGAG GAGTGTTCAG TCTCCGTGAA      60

CGTTCCCTTA GCACTCTGCC ACTTATTGGG TCAGCTGTTA ACATCAGTAC GTTAATGTTT     120

CCTGATGGTC CATGTCTGTT ACTCGCCTGT CAAGAGGCGT GACACCGGGC GTGTTCCCCA     180

GAGTGACTTT TCCTTTTATT TCCCTTCAGC TAAAATAAAG GAGGAGGAAG CTGCTAAGGA     240

CTAGTTCTGC CCTCCCGTCA CCCCTGTTTC TGGCACCAGG AATCCCCAAC ATGCACTGAT     300

GTTGTGTTTT TAACATGTCA ATCTGTCCGT TCACATGTGT GGTACATGGT GTTTGTGGCC     360

TTGGCTGACA TGAAGCTGTT GTGTGAGGTT CGCTTATCAA CTAATGATTT AGTGATCAAA     420

TTGTGCAGTA CTTTGTGCAT TCTGGATTTT AAAAGTTTTT TATTATGCAT TATATCAAAT     480

CTACCACTGT ATGAGTGGAA ATTAAGACTT TATGTAGTTT TTATATGTTG TAATATTTCT     540

TCAAATAAAT CTCTCCTATA AACCA                                          565

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:33:

AGAACTGACT TACCTCGGAT                                                  20

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:34:

AGGGTGGGTC TGTGGGAGCA                                                  20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:35:

CAGTACACAC TAGACAGGAA                                                        20

(2) INFORMATION FOR SEQ ID NO:36:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:36:

CACACTTACA GGTGCTGAAG                                                        20

(2) INFORMATION FOR SEQ ID NO:37:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:37:

GATCTCTTAC CTCGATCTTG                                                        20

(2) INFORMATION FOR SEQ ID NO:38:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:38:

CGCATCCTTA CCTCTGTCCC                                                        20

(2) INFORMATION FOR SEQ ID NO:39:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO -continued (iv) ANTI-SENSE: NO (xi) SEQUENCE DESCRIPTION: SEQ ID NO:39:

GGTGAGGTTA CCTCACAGAC                                         20

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:40:

GGCCTGACCT ACCTCCGCTC                                         20

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:41:

CCAAGGGTTA CCTTGACGGC                                         20

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:42:

AAAGATGCAA ACCTTGCTAG                                         20

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:43:

TCCATGCCTC CCTTGGGTAG                    20

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:44:

CCAGTGCTCA CTTGAACTTG                    20

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:45:

ACACAGAATC TGAAGGAAAC                    20

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:46:

AGCTTGATGC TGCAGAGAAG                    20

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:47:

ACGGGGCACC ACCTCGAGGA                    20

(2) INFORMATION FOR SEQ ID NO:48:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:48:

CTTGCCCTTC CCTGGGGGAG                                                    20

(2) INFORMATION FOR SEQ ID NO:49:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:49:

ACGGCCGCTC ACCTGCTTGG                                                    20

(2) INFORMATION FOR SEQ ID NO:50:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:50:

TCCCGGCCTG TGGGGAGAA                                                     20

(2) INFORMATION FOR SEQ ID NO:51:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:51:

GGGCCACCTA CCTGGTTATG                                                    20

(2) INFORMATION FOR SEQ ID NO:52:

(i) SEQUENCE CHARACTERISTICS:
            (A) LENGTH: 20 base pairs
            (B) TYPE: nucleic acid (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:52:

GGGTGCCATT ACCTTACAGA                                         20

(2) INFORMATION FOR SEQ ID NO:53:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:53:

ACAGGACCCA CCTTCCACGC                                         20

(2) INFORMATION FOR SEQ ID NO:54:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:54:

GCACGCGGCC CTGGGGGAAA                                         20

(2) INFORMATION FOR SEQ ID NO:55:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:55:

GCCCCACTGA CTGCCGGTGC                                         20

(2) INFORMATION FOR SEQ ID NO:56:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid

```
        (iii) HYPOTHETICAL: NO (iv) ANTI-SENSE: NO (xi) SEQUENCE DESCRIPTION: SEQ ID NO:56:

CCCGGGTGGT ATGCCGTGAG                                                    20

(2) INFORMATION FOR SEQ ID NO:57:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:57:

CTGCTCTTAC GCTTAGCCTC                                                    20

(2) INFORMATION FOR SEQ ID NO:58:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:58:

GAAGGTTCAG CTGTTTAAAG                                                    20

(2) INFORMATION FOR SEQ ID NO:59:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:59:

GTTTGGCAGG GCTGTCACAC                                                    20

(2) INFORMATION FOR SEQ ID NO:60:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: other nucleic acid (iii) HYPOTHETICAL: NO (iv) ANTI-SENSE: NO
```

(xi) SEQUENCE DESCRIPTION: SEQ ID NO:60:

CTGGCCCTAC CTGGTCTTTG                                           20

(2) INFORMATION FOR SEQ ID NO:61:

(i) SEQUENCE CHARACTERISTICS:
         (A) LENGTH: 20 base pairs
         (B) TYPE: nucleic acid
         (C) STRANDEDNESS: both
         (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:61:

CTAGCAACTC TGTCAAGCAA                                           20

(2) INFORMATION FOR SEQ ID NO:62:

(i) SEQUENCE CHARACTERISTICS:
         (A) LENGTH: 20 base pairs
         (B) TYPE: nucleic acid
         (C) STRANDEDNESS: both
         (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:62:

TAGAGCTTTA CTTTTTCATC                                           20

(2) INFORMATION FOR SEQ ID NO:63:

(i) SEQUENCE CHARACTERISTICS:
         (A) LENGTH: 20 base pairs
         (B) TYPE: nucleic acid
         (C) STRANDEDNESS: both
         (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:63:

GTTTGGGTGT TCTGTCACAG                                           20

(2) INFORMATION FOR SEQ ID NO:64:

(i) SEQUENCE CHARACTERISTICS:
         (A) LENGTH: 20 base pairs
         (B) TYPE: nucleic acid
         (C) STRANDEDNESS: both
         (D) TOPOLOGY: linear (ii) MOLECULE TYPE: other nucleic acid -continued (iii) HYPOTHETICAL: NO (iv) ANTI-SENSE: NO (xi) SEQUENCE DESCRIPTION: SEQ ID NO:64:

GTTTGGCAGC TCTGCAGGGT                                                    20